United States Patent
Anselm et al.

(10) Patent No.: US 9,896,438 B2
(45) Date of Patent: Feb. 20, 2018

(54) 2,2,2-TRIFLUOROETHYL-THIADIAZINES

(71) Applicant: Hoffmann-La Roche Inc., Little Falls, NJ (US)

(72) Inventors: Lilli Anselm, Binzen (DE); Bjoern Bartels, Schopfheim (DE); Cosimo Dolente, Allschwil (CH); Wolfgang Guba, Muellheim (DE); Haap Wolfgang, Loerrach (DE); Jens-Uwe Peters, Grenzach-Wyhlen (DE); Thomas Woltering, Freiburg (DE); Ulrike Obst Sander, Reinach (CH); Mark Rogers-Evans, Bottmingen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/502,044

(22) PCT Filed: Aug. 12, 2015

(86) PCT No.: PCT/EP2015/068506
§ 371 (c)(1),
(2) Date: Feb. 6, 2017

(87) PCT Pub. No.: WO2016/023927
PCT Pub. Date: Feb. 18, 2016

(65) Prior Publication Data
US 2017/0226091 A1 Aug. 10, 2017

(30) Foreign Application Priority Data
Aug. 15, 2014 (EP) .................................... 14181123

(51) Int. Cl.
| C07D 417/04 | (2006.01) |
| C07D 417/14 | (2006.01) |
| C07D 403/12 | (2006.01) |

(52) U.S. Cl.
CPC .................................. *C07D 403/12* (2013.01)

(58) Field of Classification Search
CPC ............................ C07D 417/04; C07D 417/14
USPC ............................................................ 544/8
See application file for complete search history.

(56) References Cited

FOREIGN PATENT DOCUMENTS

| WO | 2011044181 A1 | 4/2011 |
| WO | 2011044184 A1 | 4/2011 |

OTHER PUBLICATIONS

The International Search Report and Written Opinion, dated Sep. 23, 2015, in the related PCT Application No. PCT/EP2015/068506.

*Primary Examiner* — Kahsay Habte

(57) ABSTRACT

The present invention provides a compound of formula (I) having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

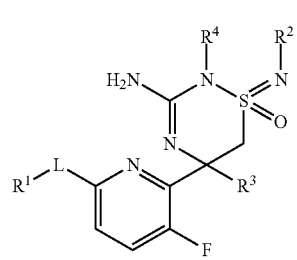

20 Claims, No Drawings

2,2,2-TRIFLUOROETHYL-THIADIAZINES

CROSS-REFERENCE TO RELATED APPLICATIONS

This application is a National Stage Application of PCT/EP2015/068506 filed Aug. 12, 2015, which claims priority from European Patent Application No, 14181123.2, filed on Aug. 15, 2014. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the micro tubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM– and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci.* 2001 March; 4(3):231-2, Roberds et al., BACE knockout mice are healthy despite lacking the primary beta-secretase activity in brain: implications for Alzheimer's disease therapeutics, *Hum Mol Genet.* 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem.* 2007 Sep. 7; 282(36): 26326). It is thus presumed that inhibitors of BACE1 activity can be useful agents for therapeutic intervention in Alzheimer's disease (AD).

WO2011044181 describes iminothiadiazine dioxides and WO2011044184 describe pentafluorosulfurimino heterocycles as BACE1 inhibitors.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, medicaments based on a compound in accordance with the invention and their production as well as the use of compounds of formula I in the control or prevention of illnesses such as Alzheimer's disease.

FIELD OF THE INVENTION

The present invention provides triazabicycles having BACE1 inhibitory properties, their manufacture, pharmaceutical compositions containing them and their use as therapeutically active substances.

SUMMARY OF THE INVENTION

The present invention provides a compound of formula I,

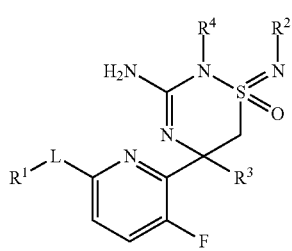

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methylpropyl), 1,2-dimethyl-propyl and the like. Particular "$C_{1-6}$-alkyl" are "$C_{1-3}$-alkyl". Specific groups are methyl and ethyl. Most specific group is methyl.

The term "halogen-$C_{1-6}$-alkyl" or "$C_{1-6}$-alkyl-halogen", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is fluoromethyl.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl (pyridyl), pyrimidinyl (pyrimidyl), pyrrolyl, quinolinyl, tetrazolyl, thiazolyl, thienyl, triazolyl, 6,7-dihydro-5H-[1]pyrindinyl and the like. Particular "heteroaryl" groups are pyridyl and pyrazinyl.

The term "aryl" denotes a monovalent aromatic carbocyclic mono- or bicyclic ring system comprising 6 to 10 carbon ring atoms. Examples of aryl moieties include phenyl and naphthyl. Particular "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. A specific acid is trifluoroacetic acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

I wherein
$R^1$ is selected from the group consisting of
  i) H,
  ii) aryl,
  iii) aryl, substituted by 1-3 substituents individually selected from cyano, halogen, $C_{1-6}$-alkyl, halogen-$C_{1-6}$-alkyl and, —O—$C_{1-6}$-alkyl, —O—$C_{2-6}$-alkynyl, —O—$C_{1-6}$-alkyl-halogen
  iv) heteroaryl, and
  v) heteroaryl, substituted by 1-3 substituents individually selected from cyano, halogen, $C_{1-6}$-alkyl, halogen-$C_{1-6}$-alkyl, —O—$C_{1-6}$-alkyl, —O—$C_{2-6}$-alkynyl, and —O—$C_{1-6}$-alkyl-halogen;

$R^2$ is selected from the group consisting of
  i) $C_{1-6}$-alkyl, and
  ii) halogen-$C_{1-6}$-alkyl;
$R^3$ is selected from the group consisting of
  i) $C_{1-6}$-alkyl, and
  ii) halogen-$C_{1-6}$-alkyl;
$R^4$ is selected from the group consisting of
  i) $C_{1-6}$-alkyl, and
  ii) halogen-$C_{1-6}$-alkyl;
L is selected from the group consisting of
  i) absent, and
  ii) —NH—C(=O)—;
or pharmaceutically acceptable salts thereof.

A certain embodiment of this invention relates to a compound of formula I as described herein, which is of formula Ia, wherein L, $R^1$, $R^2$, $R^3$ and $R^4$ are as described herein Ia A certain embodiment of this invention relates to a compound of formula I as described herein, which is of formula Ia, wherein L, $R^1$, $R^2$, $R^3$ and $R^4$ are as described herein Ia'

A certain embodiment of this invention relates to a compound of formula I as described herein, wherein $R^1$ is heteroaryl, substituted by 1-2 substituents individually selected from cyano, halogen, $C_{1-6}$-alkyl, halogen-$C_{1-6}$-alkyl, —O—$C_{1-6}$-alkyl, —O—$C_{2-6}$-alkynyl, and —O—$C_{1-6}$-alkyl-halogen.

A certain embodiment of this invention relates to a compound of formula I as described herein, wherein $R^1$ is pyridyl or pyrazinyl, substituted by 1-2 substituents individually selected from cyano, methyl, methoxy, fluoromethyoxy, trifluoroethoxy, but-2-ynoxy and prop-2-ynoxy.

A certain embodiment of this invention relates to a compound of formula I as described herein, wherein $R^1$ is 5-cyano-3-choropyridyl, 5-cyano-3-methylpyridyl, 5-cyano-pyridyl, 5-fluoro-3-methylpyridyl, 5-(fluoromethoxy)pyridyl, 5-but-2-ynoxypyrazinyl, 5-methoxypyrazinyl, 5-(2,2,2-trifluoroethoxy)pyridyl, 5-prop-2-ynoxypyridyl.

A certain embodiment of this invention relates to a compound of formula I as described herein, wherein $R^1$ is 5-cyano-3-methylpyridyl, 5-cyano-pyridyl, 5-fluoro-3-methylpyridyl, 5-(fluoromethoxy)pyridyl, 5-but-2-ynoxypyrazinyl, 5-methoxypyrazinyl, 5-(2,2,2-trifluoroethoxy)pyridyl, 5-prop-2-ynoxypyridyl.

A certain embodiment of this invention relates to a compound of formula I as described herein, wherein R is halogen-$C_{1-6}$-alkyl.

A certain embodiment of this invention relates to a compound of formula I as described herein, wherein R is 2,2,2-trifluoroethyl.

A certain embodiment of this invention relates to a compound of formula I as described herein, wherein R is $C_{1-6}$-alkyl.

A certain embodiment of this invention relates to a compound of formula I as described herein, wherein R is methyl.

A certain embodiment of this invention relates to a compound of formula I as described herein, wherein R is $C_{1-6}$-alkyl.

A certain embodiment of this invention relates to a compound of formula I as described herein, wherein R is methyl.

A certain embodiment of this invention relates to a compound of formula I as described herein, wherein $R^4$ is $C_{1-6}$-alkyl.

A certain embodiment of this invention relates to a compound of formula I as described herein, wherein $R^4$ is methyl.

A certain embodiment of this invention relates to a compound of formula I as described herein, wherein $R^4$ ishalogen-$C_{1-6}$-alkyl.

A certain embodiment of this invention relates to a compound of formula I as described herein, wherein $R^4$ is —$CH_2CF_3$.

A certain embodiment of this invention relates to an intermediate compound of formula I', wherein $R^2$, $R^3$ and $R^4$ are as described herein

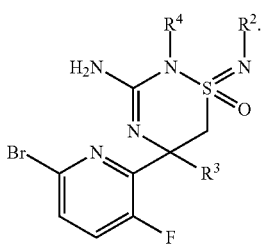

I'

A certain embodiment of this invention relates to an intermediate compound of formula A12, wherein $R^1$, $R^2$, $R^3$ and $R^4$ are as described herein

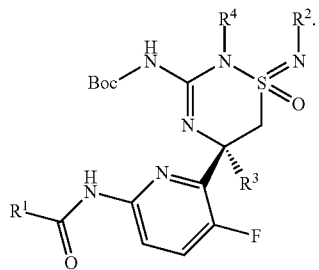

A12

A certain embodiment of this invention relates to an intermediate compound of formula II, wherein $R^2$, $R^3$ and $R^4$ are as described herein and Ar is an aryl or heteroaryl as described herein.

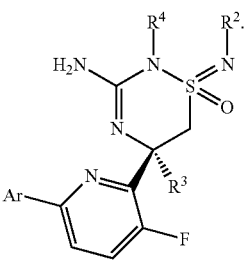

II

A certain embodiment of this invention relates to a compound of formula I", wherein $R^2$, $R^3$ and $R^4$ are as described herein

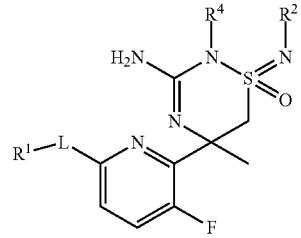

I"

A certain embodiment of this invention relates to a compound of formula I as described herein that is selected from the group consisting of
  (1R,5R)-5-(6-bromo-3-fluoro-2-pyridyl)-2,5-dimethyl-1-oxo-1-(2,2,2-trifluoroethylimino)-6H-1,2,4-thiadiazin-3-amine; 2,2,2-trifluoroacetic acid,
  (1R,5R)-5-[3-fluoro-6-(1H-pyrazol-5-yl)pyridin-2-yl]-2,5-dimethyl-1-oxo-1-(2,2,2-trifluoroethylimino)-6H-1,2,4-thiadiazin-3-amine,
  (1R,5R)-5-[6-(5-chlorothiophen-2-yl)-3-fluoropyridin-2-yl]-2,5-dimethyl-1-oxo-1-(2,2,2-trifluoroethylimino)-6H-1,2,4-thiadiazin-3-amine,
  (1S,5R)-5-(6-bromo-3-fluoropyridin-2-yl)-2,5-dimethyl-1-oxo-1-(2,2,2-trifluoroethylimino)-6H-1,2,4-thiadiazin-3-amine; 2,2,2-trifluoroacetic acid,
  (5R)-5-(6-bromo-3-fluoropyridin-2-yl)-5-methyl-1-methylimino-1-oxo-2-(2,2,2-trifluoroethyl)-6H-1,2,4-thiadiazin-3-amine; 2,2,2-trifluoroacetic acid, N-(6-((5R)-3-amino-5-methyl-1-(methylimino)-1-oxido-2-(2,2,2-trifluoroethyl)-5,6-dihydro-2H-1,2,4-thiadiazin-5yl)-5-fluoropyridin-2-yl)-3-chloro-5-cyanopicolinamide.

N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-cyano-3-methylpyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-cyanopyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-fluoro-3-methylpyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(fluoromethoxy)pyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-but-2-ynoxypyrazine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-methoxypyrazine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(2,2,2-trifluoroethoxy)pyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-prop-2-ynoxypyridine-2-carboxamide, N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide, N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide, N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]-5-fluoro-3-methylpyridine-2-carboxyamide, and N-[6-[3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide, or pharmaceutically acceptable salts thereof.

A certain embodiment of this invention relates to the 2,2,2-trifluoroacetic acid salt of a compound of formula I as described herein that is selected from the group consisting of
(1R,5R)-5-(6-bromo-3-fluoro-2-pyridyl)-2,5-dimethyl-1-oxo-1-(2,2,2-trifluoroethylimino)-6H-1,2,4-thiadiazin-3-amine; 2,2,2-trifluoroacetic acid,
(1R,5R)-5-[3-fluoro-6-(1H-pyrazol-5-yl)pyridin-2-yl]-2,5-dimethyl-1-oxo-1-(2,2,2-trifluoroethylimino)-6H-1,2,4-thiadiazin-3-amine,
(1R,5R)-5-[6-(5-chlorothiophen-2-yl)-3-fluoropyridin-2-yl]-2,5-dimethyl-1-oxo-1-(2,2,2-trifluoroethylimino)-6H-1,2,4-thiadiazin-3-amine,
(1S,5R)-5-(6-bromo-3-fluoropyridin-2-yl)-2,5-dimethyl-1-oxo-1-(2,2,2-trifluoroethylimino)-6H-1,2,4-thiadiazin-3-amine; 2,2,2-trifluoroacetic acid,
(5R)-5-(6-bromo-3-fluoropyridin-2-yl)-5-methyl-1-methylimino-1-oxo-2-(2,2,2-trifluoroethyl)-6H-1,2,4-thiadiazin-3-amine; 2,2,2-trifluoroacetic acid,
N-(6-((5R)-3-amino-5-methyl-1-(methylimino)-1-oxido-2-(2,2,2-trifluoroethyl)-5,6-dihydro-2H-1,2,4-thiadiazin-5-yl)-5-fluoropyridin-2-yl)-3-chloro-5-cyanopicolinamide.

N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-cyano-3-methylpyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-cyanopyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-fluoro-3-methylpyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(fluoromethoxy)pyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-but-2-ynoxypyrazine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-methoxypyrazine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(2,2,2-trifluoroethoxy)pyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-prop-2-ynoxypyridine-2-carboxamide, N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide, N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide, N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]-5-fluoro-3-methylpyridine-2-carboxamide, and N-[6-[3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide.

A certain embodiment of this invention relates to a compound of formula I as described herein that is selected from the group consisting of
(1R,5R)-5-(6-bromo-3-fluoro-2-pyridyl)-2,5-dimethyl-1-oxo-1-(2,2,2-trifluoroethylimino)-6H-1,2,4-thiadiazin-3-amine,
(1S,5R)-5-(6-bromo-3-fluoropyridin-2-yl)-2,5-dimethyl-1-oxo-1-(2,2,2-trifluoroethylimino)-6H-1,2,4-thiadiazin-3-amine,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-cyano-3-methylpyridine-2-carboxamide,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-cyanopyridine-2-carboxamide,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-fluoro-3-methylpyridine-2-carboxamide,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(fluoromethoxy)pyridine-2-carboxamide,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-but-2-ynoxypyrazine-2-carboxamide,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-methoxypyrazine-2-carboxamide,
N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(2,2,2-trifluoroethoxy)pyridine-2-carboxamide, N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-prop-2-ynoxypyridine-2-carboxamide, (1R,5R)-5-[3-fluoro-6-(1H-pyrazol-5-yl)pyridin-2-yl]-2,5-dimethyl-1-oxo-1-(2,2,2-trifluoroethylimino)-6H-1,2,4-thiadiazin-3-amine, and (1R,5R)-5-[6-(5-chlorothiophen-2-yl)-3-fluoropyridin-2-yl]-2,5-dimethyl-1-oxo-1-(2,2,2-trifluoroethylimino)-6H-1,2,4-thiadiazin-3-amine, or pharmaceutically acceptable salts thereof.

A certain embodiment of the invention relates to a process comprises reacting a compound of formula XI' with a compound of formula XII' to a compound of formula I.

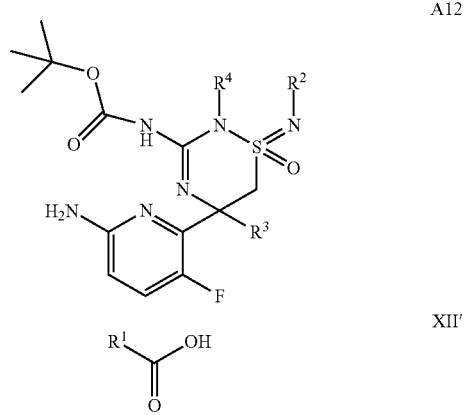

A12

XII' wherein $R^1$, $R^2$, $R^3$ and $R^4$ are as defined herein.

A certain embodiment of the invention relates to a process comprises reacting a compound of formula A10 to a compound of formula II.

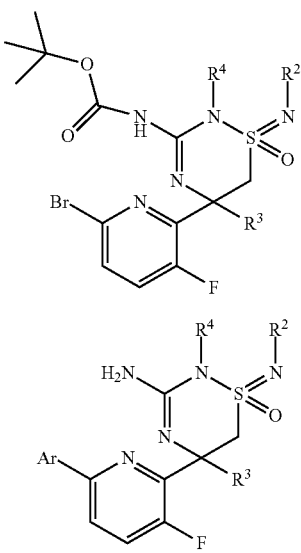

A10

II wherein $R^2$, $R^3$ and $R^4$ are as defined herein and Ar is an aryl or heteroaryl as described herein.

A certain embodiment of the invention provides a compound of formula I as described herein whenever prepared by a process as described herein.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

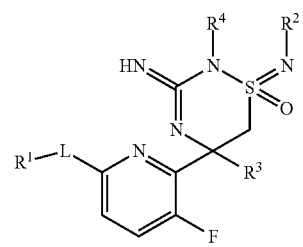

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I can be prepared through a number of synthetic routes for example as illustrated in scheme 1. The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, compounds of formula I according to the present invention can be prepared by the methods and procedures given below. Some typical procedures for the preparation of compounds of formula I are illustrated in scheme 1.

Scheme 1: Synthesis of compounds I

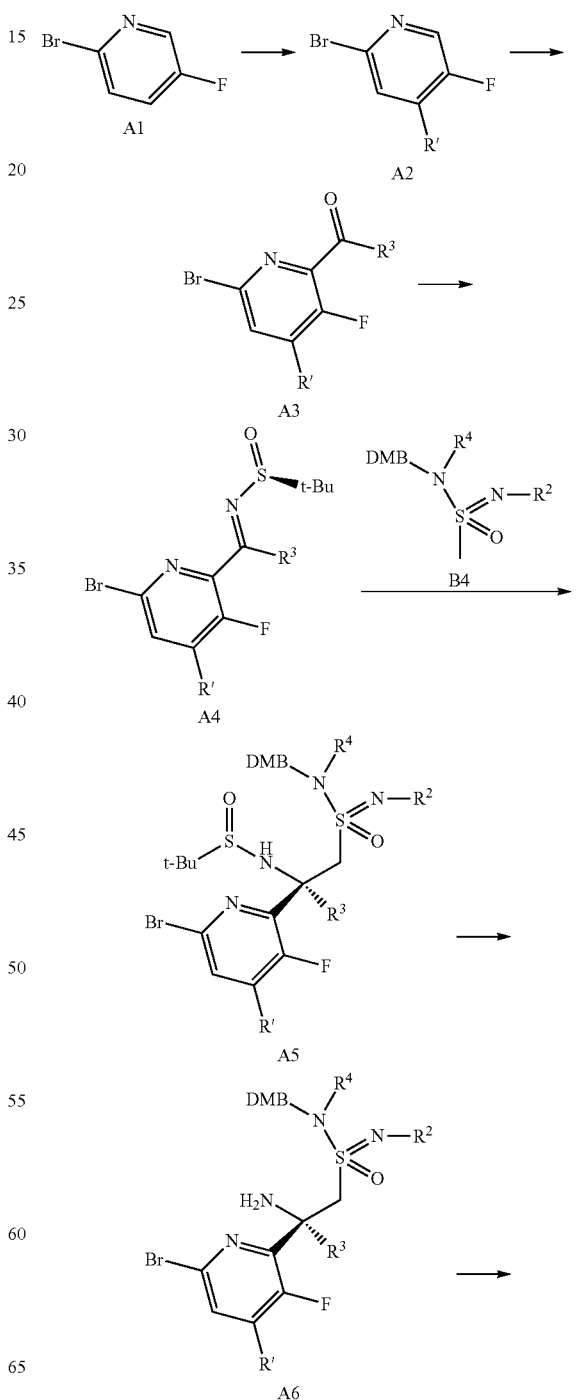

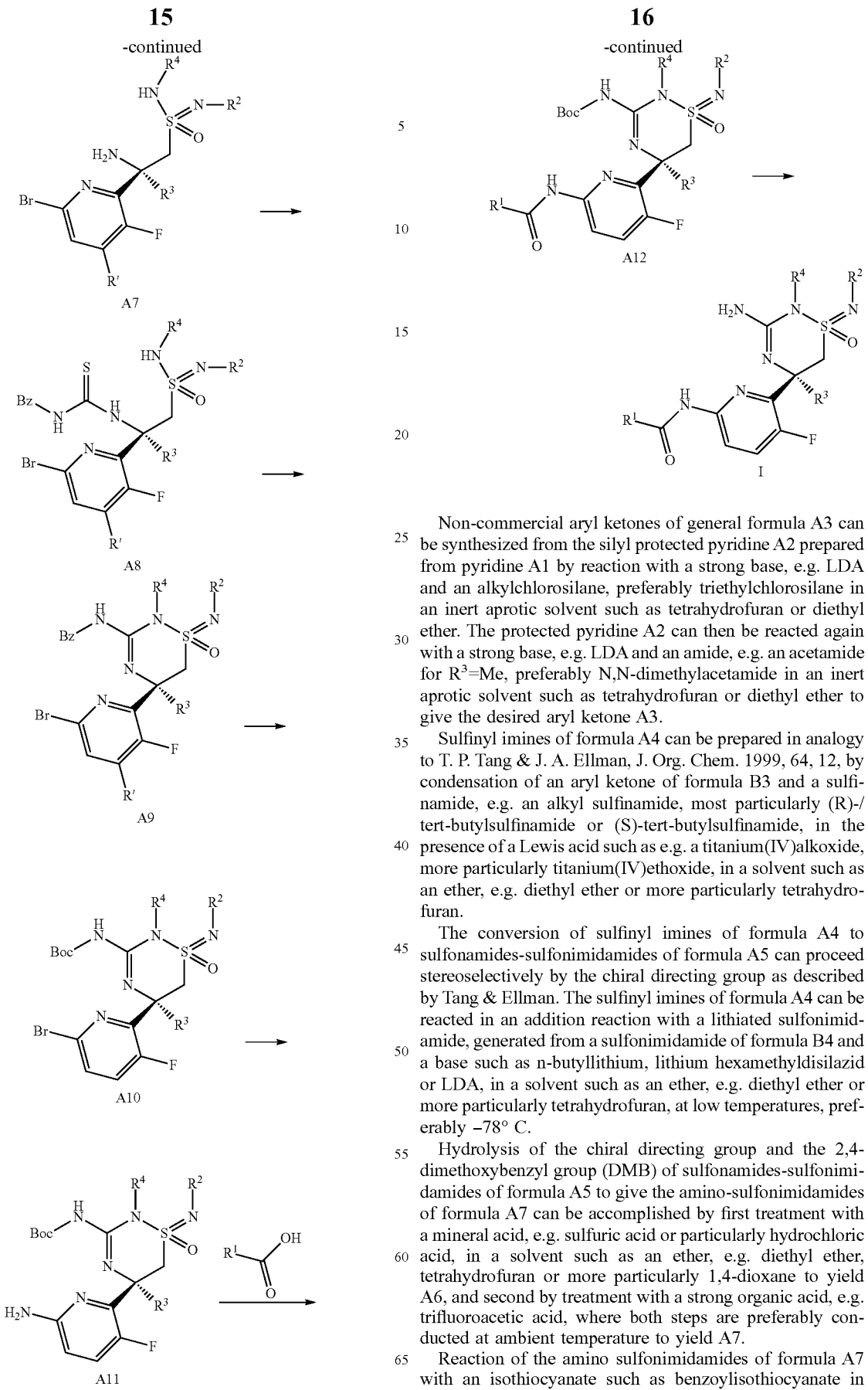

Non-commercial aryl ketones of general formula A3 can be synthesized from the silyl protected pyridine A2 prepared from pyridine A1 by reaction with a strong base, e.g. LDA and an alkylchlorosilane, preferably triethylchlorosilane in an inert aprotic solvent such as tetrahydrofuran or diethyl ether. The protected pyridine A2 can then be reacted again with a strong base, e.g. LDA and an amide, e.g. an acetamide for $R^3$=Me, preferably N,N-dimethylacetamide in an inert aprotic solvent such as tetrahydrofuran or diethyl ether to give the desired aryl ketone A3.

Sulfinyl imines of formula A4 can be prepared in analogy to T. P. Tang & J. A. Ellman, J. Org. Chem. 1999, 64, 12, by condensation of an aryl ketone of formula B3 and a sulfinamide, e.g. an alkyl sulfinamide, most particularly (R)-/tert-butylsulfinamide or (S)-tert-butylsulfinamide, in the presence of a Lewis acid such as e.g. a titanium(IV)alkoxide, more particularly titanium(IV)ethoxide, in a solvent such as an ether, e.g. diethyl ether or more particularly tetrahydrofuran.

The conversion of sulfinyl imines of formula A4 to sulfonamides-sulfonimidamides of formula A5 can proceed stereoselectively by the chiral directing group as described by Tang & Ellman. The sulfinyl imines of formula A4 can be reacted in an addition reaction with a lithiated sulfonimidamide, generated from a sulfonimidamide of formula B4 and a base such as n-butyllithium, lithium hexamethyldisilazid or LDA, in a solvent such as an ether, e.g. diethyl ether or more particularly tetrahydrofuran, at low temperatures, preferably −78° C.

Hydrolysis of the chiral directing group and the 2,4-dimethoxybenzyl group (DMB) of sulfonamides-sulfonimidamides of formula A5 to give the amino-sulfonimidamides of formula A7 can be accomplished by first treatment with a mineral acid, e.g. sulfuric acid or particularly hydrochloric acid, in a solvent such as an ether, e.g. diethyl ether, tetrahydrofuran or more particularly 1,4-dioxane to yield A6, and second by treatment with a strong organic acid, e.g. trifluoroacetic acid, where both steps are preferably conducted at ambient temperature to yield A7.

Reaction of the amino sulfonimidamides of formula A7 with an isothiocyanate such as benzoylisothiocyanate in solvents such as ethyl acetate, tetrahydrofuran or acetonitrile at temperatures between 0° C. and 80° C., preferably 23° C., affords the thiourea sulfonimidamides of formula A8.

The thiourea sulfonimidamides of formula A8 can be cyclized to the N-benzoylated amidine sulfonimidamides of formula A9 by dehydration through reaction with a carbodiimide, like e.g. dicyclohexylcarbodiimide, diisopropylcarbodiimide or A3-dimethylaminopropyl)-N'-ethylcarbodiimide hydrochloride (EDC-HCl), preferably EDC-HCl, in solvents such as ethyl acetate, tetrahydrofuran or acetonitrile, preferably acetonitrile, at temperatures between 23° C. and 100° C., preferably 80° C.

The conversion of the sulfonimidamides of formula A9 where R'=SiEt$_3$ to the desilylated sulfonimidamides of formula A10 can be effected with tetrabutylammonium fluoride or preferably potassium fluoride in the presence of an acid e.g. acetic acid in an ether or an amide preferably in a mixture of THF and dimethylformamide at ambient to elevated temperature, particularly at 23 to 40° C.

The switch of protecting groups from the N-benzoylated amidine sulfonimidamides of formula A9 to the N-tert-butoxycarbonylated amidine sulfonimidamides of formula A10 can be achieved in a two step procedure by first reaction with di-tert-butyldicarbonate (Boc$_2$O) in the presence of an amine base such as triethylamine or N-ethyl-N,N-diisopropylamine, in a solvent such as dichlormethane, tetrahydrofuran or acetonitrile, at temperatures between 0° C. and 40° C., preferably 23° C., to give the doubly acylated amidine sulfonimidamides of formula A18, and second selective removal of the benzoyl group by reaction of the doubly acylated amidine sulfonimidamides with an amine nucleophile, like e.g. diethylamine, dimethylamine or ammonia, preferably ammonia, in a solvent such as dichloromethane or tetrahydrofuran, preferably tetrahydrofuran, at temperatures between 0° C. and 40° C., preferably 23° C.

The conversion of the bromo group in formula A10 to the amine group in formula A11 can be performed by reaction with an azide, in particular sodium azide and a cooper (I) halide in particular copper (I) iodide in the presence of L-ascorbate and an alkyl-1,2-diamine in particular trans-N, N'-dimethylcyclohexane-1,2-diamine in a protic solvent such as an alcohol in particular ethanol and water at elevated temperature preferably approximately 70° C.

The coupling of the aromatic amine A11 with carboxylic acids (R$^1$—CO$_2$H) to give amides of formula A12 can be effected with T3P in an aprotic solvent such as EtOAc at ambient temperature; or alternatively the carboxylic acids (R$^1$—CO$_2$H) can be activated by using reagents such as oxalyl chloride or 1-chloro-N,N,2-trimethyl-1-propenylamine (Ghosez's reagent, CAS-no. 26189-59-3) in a chlorinated solvent such as dichloromethane at 0° C. followed by reaction with the aromatic amine A11 in the presence of an amine base such as triethylamine or diisopropylethylamine at 0° C. to ambient temperature.

The cleavage of the protecting tert-butoxy carbonyl groups in compounds of formula A12 to produce compounds of general formula I can be effected by acid, such as trifluoroacetic acid, in inert solvents, such as dichloromethane, at temperatures between 0° C. and ambient temperature.

Scheme 2: Synthesis of intermediates B4

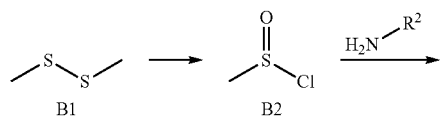

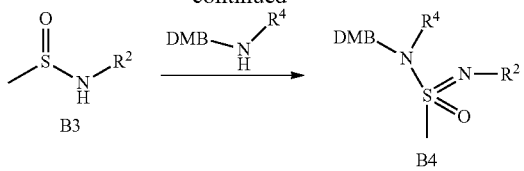

The methanesulfinyl chloride of formula B2 can be prepared by treatment of commercially available dimethyldisulfide of formula B1 with sulfuryl chloride and acetic acid at temperatures between −30° C. and 35° C. as described by Youn, Joo-Hack; Herrmann, Rudolf in *Tetrahedron Letters* 1986, 27(13), 1493-1494. The crude methanesulfinyl chloride of formula B2 can be purified by distillation or used directly in the next step to produce the sulfinamides of formula B3 which is achieved by simple reaction with an excess of an amine R$^2$—NH$_2$ or mixtures of an amine R$^2$—NH$_2$ with an amine base, such as triethylamine or N-ethyl-N,N-diisopropylamine, in a solvent such as dichlormethane or tetrahydrofuran, at temperatures starting as low as −78° C. and warming up to 0° C. or 23° C.

The sulfonimidamides of formula B4 can be prepared from the sulfinamides of formula B3 by reaction with a chlorinating reagent such as N-chlorosuccinamide or tert-butyl hypochlorite, preferably tert-butyl hypochlorite, in an inert solvent such as acetonitrile, tetrahydrofuran or dichloromethane, preferably dichloromethane, at temperatures starting as low as −78° C. and warming up to 0° C., to produce the intermediate sulfonimidoyl chlorides followed by reaction with an excess of an amine R$^4$—NHDMB or mixtures of an amine R$^4$—NHDMB with an amine base, such as triethylamine or N-ethyl-N,N-diisopropylamine at temperatures starting as low as −78° C. and warming up to 0° C. or 23° C. The amines R$^4$—NHDMB are generally prepared by a reductive amination of an amine R$^4$—NH$_2$ with 2,4-dimethoxybenzaldehyde by methods known to someone skilled in the art.

Scheme 3: Synthesis of compounds II

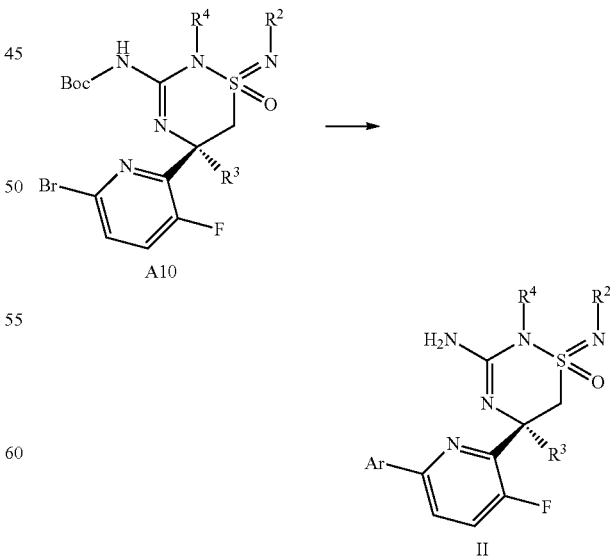

Conversion of the bromo derivative A10 to the arylated compounds of formula II can be achieved by reaction of A10 with a boronic acid or corresponding esters thereof such as pinacol ester in the presence of a base such as cesium carbonate, potassium carbonate, potassium phosphate, potassium acetate and a palladium catalyst such as tetrakis(triphenylphosphine)-palladium or 2'-(dimethylamino)-2-biphenyl-palladium(II) chloride dinorbornylphosphine complex at elevated temperature in a microwave oven between 80° C. and 120° C. in a solvent mixture of dioxane/water or acetonitrile/water. At these conditions the Boc-protecting group is thermally cleaved to directly yield compounds of formula II.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat# AL275C).

In a Perkin-Elmer White Optiplate-384 (Cat#6007290), 2 ul culture supernatants were combined with 2 μl of a 10× AlphaLISA Anti-hAβAcceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The $IC_{50}$ values were calculated using the Excel XLfit software.

TABLE 1

| | | IC$_{50}$ values | |
|---|---|---|---|
| Exam. | | Structure | BACE1 IC$_{50}$ [μM] |
| 1 | | | |
| 2 | | | |

TABLE 1-continued

| | IC$_{50}$ values | |
|---|---|---|
| Exam. | Structure | BACE1 IC$_{50}$ [µM] |
| 3 | | 0.000991 |
| 4 | | 0.002698 |

TABLE 1-continued

| | IC$_{50}$ values | |
|---|---|---|
| Exam. | Structure | BACE1 IC$_{50}$ [μM] |
| 5 | trifluoroacetic acid structure shown | 0.013943 |
| | [compound structure] | |
| 6 | trifluoroacetic acid structure shown | 0.003838 |
| | [compound structure] | |
| 7 | trifluoroacetic acid structure shown | 0.000737 |

TABLE 1-continued

| Exam. | Structure | BACE1 IC$_{50}$ [μM] |
|---|---|---|
| 8 | | 0.01012 |
| 9 | | 0.050689 |

TABLE 1-continued
| | | IC$_{50}$ values |
|---|---|---|
| Exam. | Structure | BACE1 IC$_{50}$ [µM] |
10 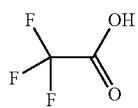

TABLE 1-continued

| | | IC$_{50}$ values |
|---|---|---|
| Exam. | Structure | BACE1 IC$_{50}$ [μM] |
| 11 | *(structure)* | |
| 12 | *(structure)* | |
| 13 | *(structure)* | 0.134165 |
| | *(structure)* | |
| 14 | *(structure)* | |

TABLE 1-continued

| | IC$_{50}$ values | |
|---|---|---|
| Exam. | Structure | BACE1 IC$_{50}$ [μM] |
| 15 | | 0.000986 |
| 16 | | 0.000593 |

TABLE 1-continued

| Exam. | Structure | BACE1 IC$_{50}$ [μM] |
|---|---|---|
| 17 | 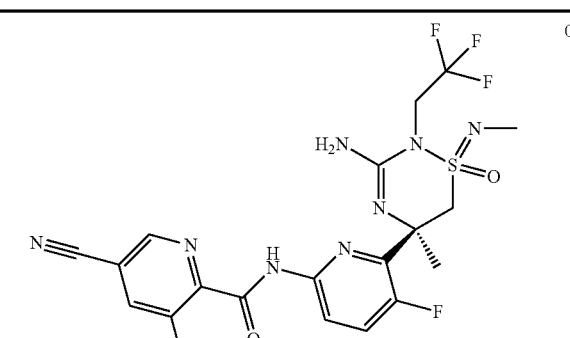 | 0.000292 |
| 18 | 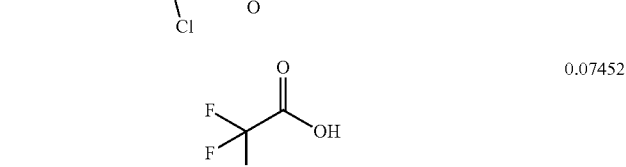 | 0.07452 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
| --- | --- |
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

Abbreviations:

Boc=tert-Butoxycarbonyl, DMB=3,3-dimethyl-1-butenyl, DCM=dichloromethane, EDCHCl=N-(3-dimethylaminopropyl)-N'-ethylcarbodiimide hydrochloride, EtOAc=Ethyl acetate, HCl=hydrogen chloride, HPLC=high performance liquid chromatography, LDA=lithium diisopropylamide, MS=mass spectrum, THF=tetrahydrofuran, and T3P=2,4,6-Tripropyl-1,3,5,2,4,6-trioxatriphosphorinane-2,4,6-trioxide.

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

LC-MS (ESI, positive or negative ion) data were recorded on Waters UPLC-MS Systems equipped with Waters Acquity, a CTC PAL auto sampler and a Waters SQD single quadrupole mass spectrometer using ES ionization modes (positive and/or negative). The separation was achieved on a Zorbax Eclipse Plus C18 1.7 µm 2.1×30 mm column at 50° C.; A=0.01% formic acid in water, B=acetonitrile at flow 1; gradient: 0 min 3% B, 0.2 min 3% B, 2 min 97% B, 1.7 min 97% B, 2.0 min 97% B. The injection volume was 2 µL. MS (ESI, positive or negative ion): FIA (flow injection analysis)-MS were recorded on an AppliedBiosystem API150 mass spectrometer. Sample introduction was made with a CTC PAL auto sampler and a Shimadzu LC-10ADVP Pump. The samples were directly flushed to the ESI source of the mass spectrometer with a flow 50 µL/min of a mixture of acetonitrile and 10 mM ammonium acetate (1:1) without a column. The injection volume was 2 µL.

SYNTHESIS OF EXAMPLES

Example 1: (1R,5R)-5-(6-bromo-3-fluoro-2-pyridyl)-2,5-dimethyl-1-oxo-1-(2,2,2-trifluoroethyl-imino)-6H-1,2,4-thiadiazin-3-amine 2,2,2-trifluoro-acetic Acid Salt a) N-(2,2,2-trifluoroethyl)methanesulfinamide

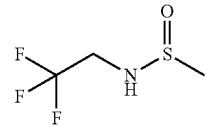

To a solution of 2,2,2-trifluoroethylamine (3.02 g, 2.41 ml, 30.4 mmol, Eq: 3) in diethyl ether (40 ml) was added dropwise at −78° C. a solution of methanesulfinic chloride (1.0 g, 10.1 mmol, Eq: 1.00) (CAS 676-85-7) in diethyl ether (5 ml). After complete addition a white precipitation was formed. The reaction mixture was allowed to warm to 0° C. and stirred at this temperature for 2 h. After 2 h stirring at room temperature the reaction was complete. The white precipitate was filtered off and the resulting filtrate was evaporated at 30° C. to yield N-(2,2,2-trifluoroethyl)methanesulfinamide as a colorless liquid (1.52 g; 93%). MS: m/z=162.0 [M+H]$^+$ b) 1-(2,4-dimethoxyphenyl)-N-methyl-N—[S-methyl-N-(2,2,2-trifluoroethyl)-sulfonimidoyl]methanamine

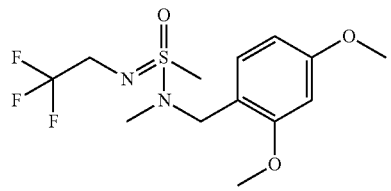 [SMILES: COc1ccc(CN(C)S(C)(=O)=NCC(F)(F)F)c(OC)c1]

Caution: t-BuOCl is light sensitive (work in a dark hood) and reacts violently with rubber, do not use rubber septum!

To a stirring solution of N-(2,2,2-trifluoroethyl)methanesulfinamide (1.5 g, 9.31 mmol, Eq: 1.00) in dry tetrahydrofurane (THF) (50 ml) at −78° C. was quickly added tert-butyl hypochlorite (1.06 g, 1.11 ml, 9.77 mmol, Eq: 1.05) and the mixture was stirred at −78° C. for 10 min. 1-(2,4-dimethoxyphenyl)-N-methylmethanamine (2.02 g, 11.2 mmol, Eq: 1.2) (CAS 102503-23-1) in THF (10 ml) were added dropwise to the reaction mixture at −78° C. followed by triethylamine (1.88 g, 2.59 ml, 18.6 mmol, Eq: 2.0) and stirred at −78° C. for 10 min. The cooling bath was replaced by an ice bath and the mixture was stirred at 0° C. for 1 h, then at 22° C. for 30 min. Saturated aqueous sodium hydrogen carbonate ($NaHCO_3$)-solution was added and stirred at room temperature for 10 min. After that the mixture was poured cautiously into 1N aqueous HCl solution, diluted with ethyl acetate, and the phases were separated. The organic layer was washed with brine, dried over sodium sulfate ($Na_2SO_4$), filtered and evaporated to dryness. The crude material was purified by flash chromatography (silica gel, 40 g, 25% to 60% ethyl acetate (EtOAc) in heptane) to yield the title compound as a white solid (2.56 g; 80.8%). MS (ESI): m/z=341.2 [M+H]$^+$ c) (S,E)-N-(1-(6-Bromo-3-fluoro-4-(triethylsilyl) pyridin-2-yl)ethylidene)-2-methylpropane-2-sulfinamide

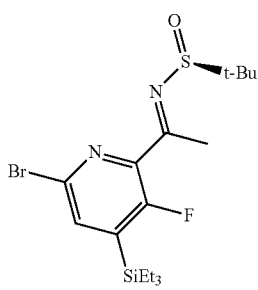

To a solution of 1-(6-bromo-3-fluoro-4-(triethylsilyl)pyridin-2-yl)ethanone, prepared according to Badiger, S. et al., int. patent application WO 2012095469A1, (8.13 g) in THF (59 ml) was added subsequently at 22° C. (S)-(−)-tert-butylsulfinamide (3.26 g) and titanium(IV)ethoxide (11.2 g) and the solution was stirred at 60° C. for 6 h. The mixture was cooled to 22° C., treated with brine, the suspension was stirred for 10 min and filtered over dicalite. The layers were separated, the aqueous layer was extracted with ethyl acetate, the combined organic layers were washed with water, dried and evaporated. The residue was purified by flash chromatography ($SiO_2$, n-heptane/EtOAc, 5:1) to give the title compound (7.5 g, 70%) as a yellow oil. MS (ESI): m/z=435.3, 437.3 [M+H]$^+$.

d) N-[(1R)-1-(6-bromo-3-fluoro-4-triethylsilyl-2-pyridyl)-2-[S-[(2,4-dimethoxyphenyl)methyl-methyl-amino]-N-(2,2,2-trifluoroethyl)sulfonimidoyl]-1-methyl-ethyl]-2-methyl-propane-2-sulfinamide

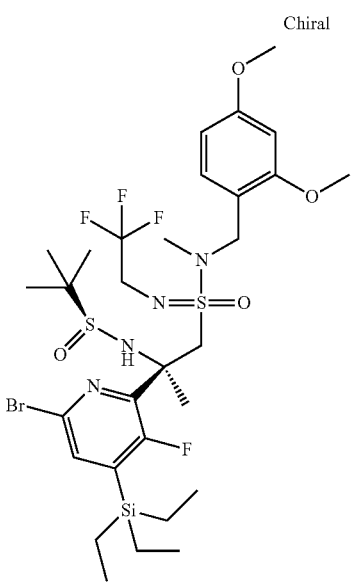 [SMILES: CC[Si](CC)(CC)c1cc(Br)nc([C@](C)(CS(=O)(=NCC(F)(F)F)N(C)Cc2ccc(OC)cc2OC)N[S@@](=O)C(C)(C)C)c1F]

To a solution of 1-(2,4-dimethoxyphenyl)-N-methyl-N—[S-methyl-N-(2,2,2-trifluoroethyl)-sulfonimidoyl]methanamine (example 1b) (7.97 g, 23.4 mmol, Eq: 1.4) in THF (100 ml) at −78° C. was added n-BuLi (1.6M in hexane) (20.7 ml, 33.1 mmol, Eq: 1.98) dropwise. The clear solution was stirred at −78° C./−40° C. for 2.5 h (The reaction mixture was allowed to come after 1 h to −40° C., stirred at this temperature for 0.5 h and then at −78° C. for remaining time). A solution of (S,E)-N-(1-(6-bromo-3-fluoro-4-(triethylsilyl)pyridin-2-yl)ethylidene)-2-methylpropane-2-sulfinamide (example 1c) (7.28 g, 16.7 mmol, Eq: 1.00) in THF (50 ml) was added dropwise so that temperature remained at between −78° C. and −73° C. The reaction mixture was stirred at −78° C. for 3 h, then quenched at −78° C. with sat. aqueous ammonium chloride ($NH_4Cl$)-solution (80 ml) and water (100 ml), followed by extraction with AcOEt (3×500 ml). The combined organic extracts were washed with brine, dried over $Na_2SO_4$, filtered off and evaporated to give a brownish oil. The crude material was purified by flash chromatography (silica gel, 120 g, 10% to 50% EtOAc in heptane) to yield the title compound as a colorless viscous oil (2.14 g; 17%). MS (ESI): m/z=[M+H]$^+$. $^1$H NMR (300 MHz, CHLOROFORM-d) 0.77-1.05 (m, 15H) 1.16-1.32 (m, 9H) 1.92 (s, 3H) 2.78 (s, 3H) 3.22-3.71 (m, 2H) 3.82 (6H) 3.92 (d, J=14.33 Hz, 1H) 4.14 (d, J=14.13 Hz, 1H) 4.24-4.29 (d, 1H) 4.39-4.44 (d, 1H) 5.81 (s, 1H) 6.51 (m, 2H) 6.45-6.51 (m, 2H) 7.15-7.23 (m, 1H) 7.30-7.44 (m, 1H) 7.38 (d, 1H).

e) (2R)-2-(6-bromo-3-fluoro-4-triethylsilyl-2-pyridyl)-1-[S-[(2,4-dimethoxyphenyl)methyl-methyl-amino]-N-(2,2,2-trifluoroethyl)sulfonimidoyl]propan-2-amine

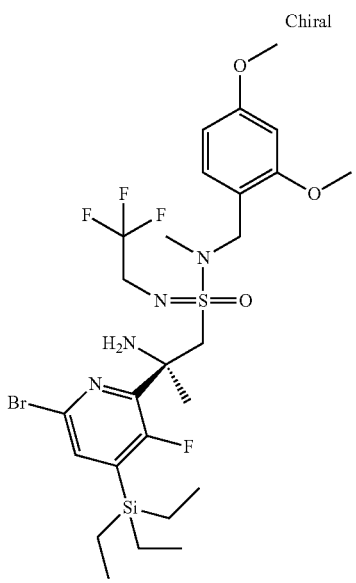 [SMILES: CC[Si](CC)(CC)c1cc(Br)nc([C@@](C)(N)CS(=O)(=NCC(F)(F)F)N(C)Cc2ccc(OC)cc2OC)c1F]

To a stirred solution of example 1d) (2.1 g, 2.71 mmol, Eq: 1.00) in THF (20 ml) was added HCl solution (37% in water) (1.33 g, 1.11 ml, 13.5 mmol, Eq: 5) at 25° C. and stirred for 2 h. The crude mixture was evaporated and the residue was extracted with AcOEt (250 ml)/saturated aqueous NaHCO₃-solution (100 ml), the aqueous layer was back-extracted with EtOAc (3×100 mL). The organic layers were combined, washed with saturated aqueous NaCl solution (1×100 mL), dried over magnesium sulfate (MgSO₄) and concentrated in vacuo to yield the title compound as a colorless viscous oil (1.75 g; 96%). MS (ESI): m/z=673.2 [M+H]⁺.

f) (2R)-2-(6-bromo-3-fluoro-4-triethylsilyl-2-pyridyl)-1-[S-(methylamino)-N-(2,2,2-trifluoroethyl)sulfonimidoyl]propan-2-amine

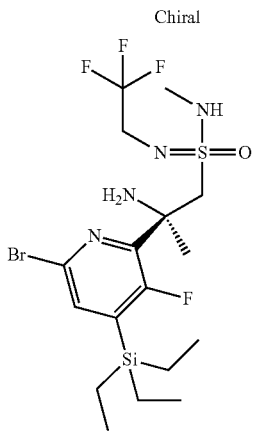 [SMILES: CC[Si](CC)(CC)c1cc(Br)nc([C@@](C)(N)CS(=O)(=NCC(F)(F)F)NC)c1F]

To a stirring solution of example 1e) (1.75 g, 2.61 mmol, Eq: 1.00) in dichloromethane (10 ml) was added at 25° C. TFA (14.9 g, 10.0 ml, 130 mmol, Eq: 50). The mixture was stirred for 1 h. After addition of trifluoro acetic acid (TFA) and stirring for approximately 15 min. a bright pink solution was formed. The reaction mixture was adjusted with ice-cold aqueous 10%-Na₂CO₃-solution (80 ml) to pH=8-9, extracted with dichloromethane (250 ml), the aqueous layer was back-extracted with dichloromethane (3×100 mL). The organic layers were combined, washed with brine (1×100 mL), dried over MgSCO₄ and concentrated in vacuo to yield a light yellow waxy solid (1.4 g; 100%). MS (ESI): m/z=523.1 [M+H]⁺.

g) N-[[(1R)-1-(6-bromo-3-fluoro-4-triethylsilyl-2-pyridyl)-1-methyl-2-[S-(methylamino)-N-(2,2,2-trifluoroethyl)sulfonimidoyl]ethyl]carbamothioyl]benzamide

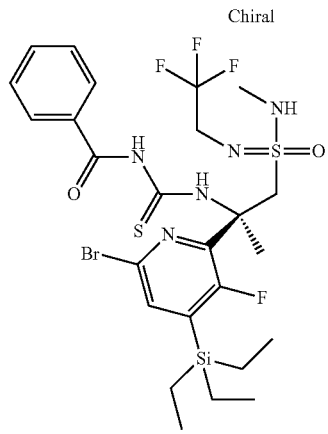 [SMILES: CC[Si](CC)(CC)c1cc(Br)nc([C@](C)(CS(=O)(=NCC(F)(F)F)NC)NC(=S)NC(=O)c2ccccc2)c1F]

In a 10 mL round-bottomed flask, (2R)-2-amino-2-(6-bromo-3-fluoro-4-(triethylsilyl)pyridin-2-yl)-N-methyl-N'-(2,2,2-trifluoroethyl)propane-1-sulfonimidamide (example 1f), 0.205 g, 393 µmol, Eq: 1.00) was combined with THF (2.4 ml) to give a light yellow thin suspension. Benzoyl isothiocyanate (70.6 mg, 58.1 µl, 432 µmol, Eq: 1.1) was added and the dark yellow suspension was stirred at room temperature for 1.5 h. The reaction mixture was diluted with methynol (MeOH) (1 ml) and the formed precipitate was filtered off, the resulting filtrate was evaporated. The crude material was subsequently purified by flash chromatography (silica gel, 12 g, 0% to 40% EtOAc in n-heptane) to yield the title compound as a colorless amorphous solid (214 mg; 79%). MS (ESI): m/z=682.3 [M+H]⁺.

h) N-[(1R,5R)-5-(6-bromo-3-fluoro-4-triethylsilyl-2-pyridyl)-2,5-dimethyl-1-oxo-1-(2,2,2-trifluoroethylimino)-6H-1,2,4-thiadiazin-3-yl]benzamide and N-[(1S,5R)-5-(6-bromo-3-fluoro-4-triethylsilyl-2-pyridyl)-2,5-dimethyl-1-oxo-1-(2,2,2-trifluoroethylethylimino)-6H-1,2,4-thiadiazin-3-yl]benzamide

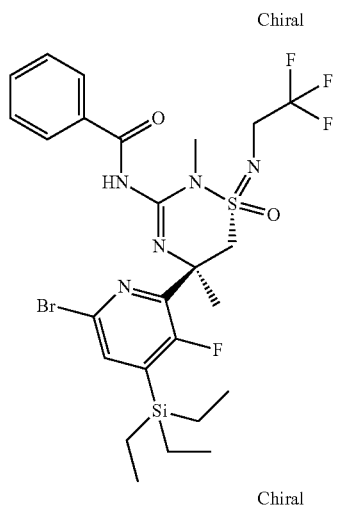

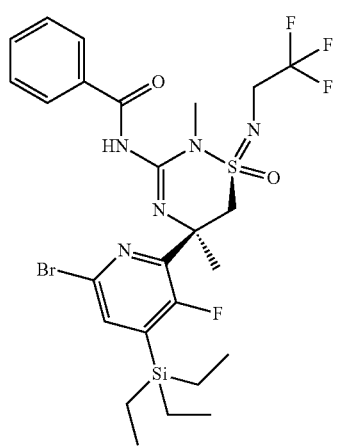

To a solution of N-((2R)-2-(6-bromo-3-fluoro-4-(triethylsilyl)pyridin-2-yl)-1-(N-methyl-N'-(2,2,2-trifluoroethyl)sulfamimidoyl)propan-2-ylcarbamothioyl)benzamide (example 1g), 0.210 g, 307 µmol, Eq: 1.00) in acetonitrile (2.9 ml) was added at room temperature N-1-((ethylimino)methylene)-N,N-dimethylpropane-1,3-diamine (EDC) (71.4 mg, 81.4 µl, 460 µmmol, Eq: 1.5) and stirred at 80° C. for 1.5 h. The light yellow solution was evaporated. The crude material was purified by flash chromatography (silica gel, 12 g, 0% to 40% EtOAc in n-heptane) to yield the title compounds as colorless amorphous solids as a mixture of diastereomers (80 mg; 40%; N-[(1R,5R)-5-(6-bromo-3-fluoro-4-triethylsilyl-2-pyridyl)-2,5-dimethyl-1-oxo-1-(2,2,2-trifluoroethylimino)-6H-1,2,4-thiadiazin-3-yl]benzamide and 102 mg; 51% N-[(1S,5R)-5-(6-bromo-3-fluoro-4-triethylsilyl-2-pyridyl)-2,5-dimethyl-1-oxo-1-(2,2,2-trifluoroethylimino)-6H-1,2,4-thiadiazin-3-yl]benzamide). MS (ESI): m/z=652.2 [M+H]$^+$.

i) N-[(1R,5R)-5-(6-bromo-3-fluoro-2-pyridyl)-2,5-dimethyl-1-oxo-1-(2,2,2-trifluoroethylimino)-6H-1,2,4-thiadiazin-3-yl]benzamide

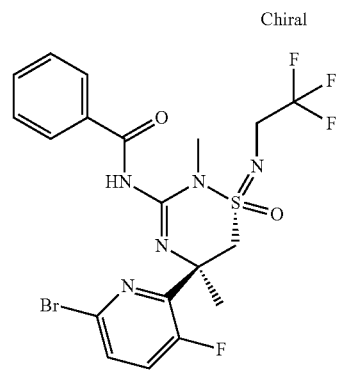 [SMILES: CN1C(NC(=O)c2ccccc2)=N[C@](C)(c2nc(Br)ccc2F)C[S@@]1(=O)=NCC(F)(F)F]

To a solution of N-[(1R,5R)-5-(6-bromo-3-fluoro-4-triethylsilyl-2-pyridyl)-2,5-dimethyl-1-oxo-1-(2,2,2-trifluoroethylimino)-6H-1,2,4-thiadiazin-3-yl]benzamide (example 1h), 0.08 g, 123 µmol, Eq: 1.00) in dry THF (0.8 ml) and DMF (0.8 ml) was added at room temperature acetic acid (14.8 mg, 14.1 µl, 246 µmol, Eq: 2) and potassium fluoride (14.3 mg, 246 µmol, Eq: 2) and the formed white suspension was stirred at room temperature for 1 h. The reaction mixture was evaporated, the residue was extracted with AcOEt (20 ml)/aqueous saturated NaHCO$_3$-solution (5 ml).The aqueous layer was back-extracted with EtOAc (3×15 ml). The organic layers were combined, washed with sat NaCl (1×5 ml), were dried over Na$_2$SO$_4$ and concentrated in vacuo to yield the title compound as a white solid (0.06 g; 91%). MS (ESI): m/z=538.1 [M+H]$^+$.

j) tert-butyl N-[(1R,5R)-5-(6-bromo-3-fluoro-2-pyridyl)-2,5-dimethyl-1-oxo-1-(2,2,2-trifluoroethylimino)-6H-1,2,4-thiadiazin-3-yl]carbamate

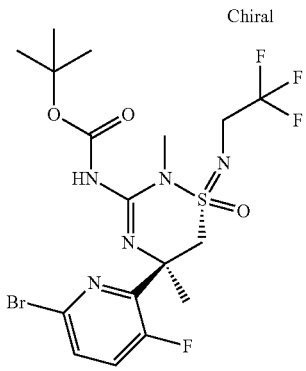 [SMILES: CN1C(NC(=O)OC(C)(C)C)=N[C@](C)(c2nc(Br)ccc2F)C[S@@]1(=O)=NCC(F)(F)F]

l) To a stirring solution of N-[(1R,5R)-5-(6-bromo-3-fluoro-2-pyridyl)-2,5-dimethyl-1-oxo-1-(2,2,2-trifluoroethylimino)-6H-1,2,4-thiadiazin-3-yl]benzamide (example 1i), 0.060 g, 112 µmol, Eq: 1.00) in THF (800 µl) was added at room temperature triethylamine (24.9 mg, 34.3 µl, 246 µmol, Eq: 2.2) and 4-(Dimethylamino)-pyridinyl (DMAP) (2.73 mg, 22.4 µmol, Eq: 0.2) followed by the addition of Boc$_2$O (53.7 mg, 246 µmol, Eq: 2.2). The reaction mixture was stirred for 3 h. The dark yellow crude reaction mixture was evaporated to dryness.

The residue was dissolved in methanol (500 μl) and ammonia (7N in MeOH) (799 μl, 5.59 mmol, Eq: 50) was added at room temperature. The formed light brownish solution was stirred for 15 min. The reaction mixture was evaporated and subsequently purified by flash chromatography (silica gel, 4 g, 0% to 30% EtOAc in n-heptane) to yield the title compound as a colorless amorphous solid (0.043 g; 72%). MS (ESI): m/z=534.1 [M+H]$^+$.

k) (1R,5R)-5-(6-bromo-3-fluoro-2-pyridyl)-2,5-dimethyl-1-oxo-1-(2,2,2-trifluoroethylimino)-6H-1,2,4-thiadiazin-3-amine 2,2,2-trifluoroacetic acid salt To a stirring solution of tert-butyl N-[(1R,5R)-5-(6-bromo-3-fluoro-2-pyridyl)-2,5-dimethyl-1-oxo-1-(2,2,2-trifluoroethylimino)-6H-1,2,4-thiadiazin-3-yl]carbamate (example 1j); 0.002 g, 3.76 μmol, Eq: 1.00) in dichloromethane (60 μL) was added at room temperature TFA (85.7 mg, 57.9 μL, 751 μmol, Eq: 200) and stirred for 2 h. The reaction mixture was concentrated in vacuo to yield the title compound as a amorphous, colorless solid (2.18 mg; 106%). MS (ESI): m/z=434.1 [M+H]$^+$.

Example 2: (1S,5R)-5-(6-bromo-3-fluoro-2-pyridyl)-2,5-dimethyl-1-oxo-1-(2,2,2-trifluoroethylimino)-6H-1,2,4-thiadiazin-3-amine 2,2,2-trifluoroacetic Acid Salt Example 2 was prepared from N-[(1S,5R)-5-(6-bromo-3-fluoro-4-triethylsilyl-2-pyridyl)-2,5-dimethyl-1-oxo-1-(2,2,2-trifluoroethylimino)-6H-1,2,4-thiadiazin-3-yl]benzamide (example 1h) in analogy to the methods described in examples 1k) to yield the title compound as a colorless amorphous solid (3.32 mg; 100%). MS (ESI): m/z=434.1 [M+H]$^+$.

Example 3

N-[6-[(1R,5R)-3-amino-2,5-dimethyl-1-oxo-1-(2,2,2-trifluoroethylimino)-6H-1,2,4-thiadiazin-5-yl]-5-fluoro-2-pyridyl]-5-cyano-3-methyl-pyridine-2-carboxamide 2,2,2-trifluoroacetic Acid Salt tert-Butyl N-[(1R,5R)-5-(6-amino-3-fluoro-2-pyridyl)-2,5-dimethyl-1-oxo-1-(2,2,2-trifluoroethylimino)-6H-1,2,4-thiadiazin-3-yl]carbamate In a 10 ml round-bottomed flask, example 1k) (0.075 g, 141 μmol, Eq: 1.00) was combined with dioxane (350 μl) and water (100 μl) to give a colorless solution. To this solution was added at 25° C. sodium azide (73.3 mg, 1.13 mmol, Eq: 8), copper (I) iodide (10.7 mg, 56.4 μmol, Eq: 0.4), sodium ascorbate (11.2 mg, 56.4 μmol, Eq: 0.4) followed by trans-N,N'-dimethylcyclohexane-1,2-diamine (12.0 mg, 13.3 μL, 84.5 μmol, Eq: 0.6). The dark green reaction mixture was heated to 70° C. and stirred for 45 min. The reaction mixture was quenched with aqueous saturated NaHCO$_3$-solution and extracted 3× with AcOEt (2 ml). The organic layer were combined and washed with brine, dried over Na$_2$SO$_4$ and concentrated in vacuo. The crude material was purified by flash chromatography (silica gel, 4 g, 5% to 40% EtOAc in n-heptane) to yield the title compound as colorless amorphous solid (51 mg; 77%). MS (ESI): m/z=469.2 [M+H]$^+$.

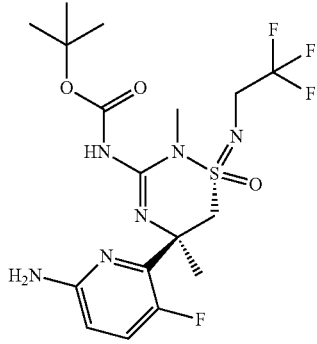 [SMILES: CN1C(NC(=O)OC(C)(C)C)=N[C@](C)(c2nc(N)ccc2F)C[S@@]1(=O)=NCC(F)(F)F]

a) tert-Butyl N-[(1R,5R)-5-[6-[(5-cyano-3-methyl-pyridine-2-carbonyl)amino]-3-fluoro-2-pyridyl]-2,5-dimethyl-1-oxo-1-(2,2,2-trifluoroethylimino)-6H-1,2,4-thiadiazin-3-yl]carbamate

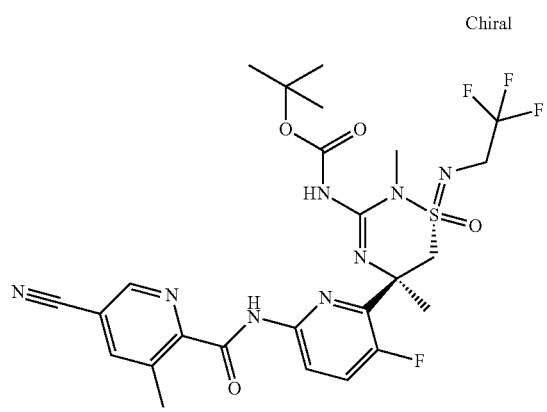 [SMILES: Cc1cc(C#N)cnc1C(=O)Nc1ccc(F)c([C@]2(C)C[S@@](=O)(=NCC(F)(F)F)N(C)C(NC(=O)OC(C)(C)C)=N2)n1]

Chiral

To a suspension of 5-cyano-3-methylpicolinic acid (1.33 mg, 8.2 μmol, Eq: 1.2) in dichloromethane (100 μl) was added at 0° C. 1-chloro-N,N-2-trimethylprop-1-en-1-amine (1.14 mg, 1.13 μl, 8.54 μmol, Eq: 1.25). and the formed colorless suspension was stirred at 0° C. 20 min. A solution of tert-Butyl N-[(1R,5R)-5-(6-amino-3-fluoro-2-pyridyl)-2,5-dimethyl-1-oxo-1-(2,2,2-trifluoroethylimino)-6H-1,2,4-thiadiazin-3-yl]carbamate (3.2 mg, 6.83 μmol, Eq: 1.00) in dichloromethane (146 μl) was added to above reaction mixture at 0° C. and the resulting yellow solution was stirred at room temperature for 60 min. The reaction mixture was concentrated in vacuo. The residue was purified by flash chromatography (4 g silica-gel, isocratically 40% AcOEt in n-heptane) to yield the title compound as a colorless amorphous solid (3.8 mg; 91%). MS (ESI): m/z=613.2 [M+H]$^+$.

b) N-[6-[(1R,5R)-3-amino-2,5-dimethyl-1-oxo-1-(2,2,2-trifluoroethylimino)-6H-1,2,4-thiadiazin-5-yl]-5-fluoro-2-pyridyl]-5-cyano-3-methyl-pyridine-2-carboxamide 2,2,2-trifluoro-acetic Acid Salt To a stirring solution of tert-Butyl N-[(1R,5R)-5-(6-amino-3-fluoro-2-pyridyl)-2,5-dimethyl-1-oxo-1-(2,2,2-trifluoroethylimino)-6H-1,2,4-thiadiazin-3-yl]carbamate (3.8 mg, 6.2 μmol, Eq: 1.00) in dichloromethane (70 μl) was added at room temperature TFA (106 mg, 71.7 μl, 930 μmol, Eq: 150) and stirred for 30 min. The reaction mixture was concentrated in vacuo to yield the title compound as a colorless amorphous solid (4.05 mg; 100%). MS (ESI): m/z=513.2 [M+H]$^+$.

Example 4: N-[6-[(1R,5R)-3-amino-2,5-dimethyl-1-oxo-1-(2,2,2-trifluoroethylimino)-6H-1,2,4-thiadiazin-5-yl]-5-fluoro-2-pyridyl]-5-cyano-pyridine-2-carboxamide 2,2,2-trifluoroacetic Acid Salt Example 4 was prepared in analogy to the methods described for example 3 starting from 5-cyanopicolinic acid to yield the title compound as a colorless amorphous solid (11.8 mg; 100%). MS (ESI): m/z=499.2 [M+H]$^+$.

Example 5: N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-fluoro-3-methyl-pyridine-2-carboxamide 2,2,2-trifluoroacetic Acid Salt Example 5 was prepared in analogy to the methods described for example 3 starting from 5-fluoro-2-methylpicolinic acid to yield the title compound as a colorless amorphous solid (16.6 mg; 100%). MS (ESI): m/z=506.3 [M+H]$^+$.

Example 6: N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(fluoromethoxy)pyridine-2-carboxamide 2,2,2-trifluoroacetic Acid Salt Example 6 was prepared in analogy to the methods described for example 3 starting from 5-(fluoromethoxy)pyridine-2-carboxylic acid to yield the title compound as a light brown amorphous solid (16.6 mg; 100%). MS (ESI): m/z=522.2 [M+H]$^+$.

Example 7: N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-but-2-ynoxypyrazine-2-carboxamide; 2,2,2-trifluoroacetic Acid Example 7 was prepared in analogy to the methods described for example 3 starting from 5-but-2-ynoxypyrazine-2-carboxylic acid to yield the title compound as a light brown amorphous solid (11.9 mg; 100%). MS (ESI): m/z=543.2 [M+H]$^+$.

Example 8: N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-methoxypyrazine-2-carboxamide 2,2,2-trifluoroacetic Acid Salt Example 8 was prepared in analogy to the methods described for example 3 starting from 5-methoxypyrazine-2-carboxylic acid to yield the title compound as a light brown amorphous solid (13.1 mg; 100%). MS (ESI): m/z=505.2 [M+H]$^+$.

Example 9: N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-(2,2,2-trifluoroethoxy)pyridine-2-carboxamide 2,2,2-trifluoroacetic Acid Salt Example 9 was prepared in analogy to the methods described for example 3 starting from 5-(2,2,2-trifluoroethoxy)pyridine-2-carboxylic acid to yield the title compound as a light brown amorphous solid (3.92 mg; 95%). MS (ESI): m/z=572.1 [M+H]$^+$.

Example 10: N-[6-[(1R,5R)-3-amino-2,5-dimethyl-1-oxo-1-(2,2,2-trifluoroethylimino)-6H-1,2,4-thiadiazin-5-yl]-5-fluoropyridin-2-yl]-5-prop-2-ynoxypyridine-2-carboxamide 2,2,2-trifluoroacetic Acid Salt Example 10 was prepared in analogy to the methods described for example 3 starting from 5-prop-2-ynoxypyridine-2-carboxylic acid to yield the title compound as a light brown amorphous solid (31 mg; 100%). MS (ESI): m/z=528.2 [M+H]$^+$.

Example 11: (1R,5R)-5-[3-fluoro-6-(1H-pyrazol-5-yl)pyridin-2-yl]-2,5-dimethyl-1-oxo-1-(2,2,2-trifluoroethylimino)-6H-1,2,4-thiadiazin-3-amine In a microwave-tube tert-butyl N-[(1R,5R)-5-(6-bromo-3-fluoro-2-pyridyl)-2,5-dimethyl-1-oxo-1-(2,2,2-trifluoroethylimino)-6H-1,2,4-thiadiazin-3-yl]carbamate (example 1j) (30 mg, 56.4 µmol, Eq: 1.00) was combined with acetonitrile (340 µl) and water (340 µl) to give a colorless solution. It was added potassium acetate (16.6 mg, 169 µmol, Eq: 3.00) and 5-(4,4,5,5-tetramethyl-1,3,2-dioxaborolan-2-yl)-1H-pyrazole (13.1 mg, 67.6 µmol, Eq: 1.2) to give a suspension and then finally under a nitrogen atmosphere tetrakis(triphenylphosphine)palladium (0) (6.51 mg, 5.64 µmol, Eq: 0.1) was added. The MW-tube was closed and heated in the microwave at 140° C. for 20 min. The reaction mixture was purified by preparative HPLC to yield the title compound as a colorless amorphous solid (5.14 mg; 22%). MS (ESI): m/z=420.2 [M+H]$^+$.

Example 12: (1R,5R)-5-[6-(5-chlorothiophen-2-yl)-3-fluoropyridin-2-yl]-2,5-dimethyl-1-oxo-1-(2,2,2-trifluoroethylimino)-6H-1,2,4-thiadiazin-3-amine In a microwave-tube tert-butyl N-[(1R,5R)-5-(6-bromo-3-fluoro-2-pyridyl)-2,5-dimethyl-1-oxo-1-(2,2,2-trifluoroethylimino)-6H-1,2,4-thiadiazin-3-yl]carbamate (example 1j) (30 mg, 56.4 µmol, Eq: 1.00) was combined with dioxane (340 µl) and water (340 µl) to give a colorless solution. It was added tripotassium phosphate (35.9 mg, 169 µmol, Eq: 3) and 5-chlorothiophen-2-ylboronic acid (11.0 mg, 67.6 µmol, Eq: 1.2) to give a suspension and then finally under a nitrogen atmosphere 2'-(dimethylamino)-2-biphenyl-palladium(II) chloride dinorbornylphosphine complex (3.16 mg, 5.64 µmol, Eq: 0.1).The MW-tube was closed and heated in the microwave at 120° C. for 300 min. The crude reaction mixture was purified by preparative HPLC to yield the title compound as a light yellow solid (8.39 mg; 32%). MS (ESI): m/z=570.1 [M+H]$^+$.

Example 13: N-[6-[3-amino-5-methyl-1-methylimino-1-oxo-2-(2,2,2-trifluoroethyl)-6H-1,2,4-thiadiazin-5-yl]-5-fluoropyridin-2-yl]-5- cyano-3-methyl-pyridine-2-carboxamide; 2,2,2-trifluoroacetic Acid a) N-[(2,4-dimethoxyphenyl)methyl]-N—(N,S-dimethylsulfonimidoyl)-2,2,2-trifluoro-ethanamine

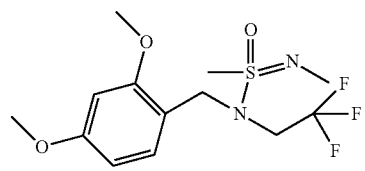 [SMILES: CN=S(C)(=O)N(Cc1ccc(OC)cc1OC)CC(F)(F)F]

To a stirred solution of methanesulfinic acid methylamide (CAS 18649-17-7) (2.4 g, 25.806 mmol) in THF (30 ml) at 0° C. tBuOCl (4.3 ml, 38.71 mmol) was added dropwise under dark and stirred the reaction mixture for 2 h at same temperature. To this mixture (2,4-dimethoxy-benzyl)-(2,2,2-trifluoro-ethyl)-amine (CAS 1016734-11-4) (8.3 g, 33.548 mmol) and $Cs_2CO_3$ (18.2 g, 51.613 mmol) were added respectively and stirred the solution for 16 h at 25° C. The reaction was quenched with water and extracted with dichloromethane (3 times). The combined organic layer was washed with brine solution, dried over anhydrous $Na_2SO_4$, evaporated under reduced pressure to get crude product which was purified by silica gel column chromatography using 0-25% EtOAc-hexane as eluting solvent to get N-[(2,4-dimethoxyphenyl)methyl]-N—(N,S-dimethylsulfonimidoyl)-2,2,2-trifluoro-ethanamine as colorless liquid (2 g, 22.8%). m/z=341.2 [M+H]$^+$.

b) N-[2-(6-bromo-3-fluoro-4-triethylsilylpyridin-2-yl)-1-[S-[(2,4-dimethoxyphenyl)methyl-(2,2,2-trifluoroethyl)amino]-N-methylsulfonimidoyl]propan-2-yl]-2-methylpropane-2-sulfinamide; mixture of diastereomers

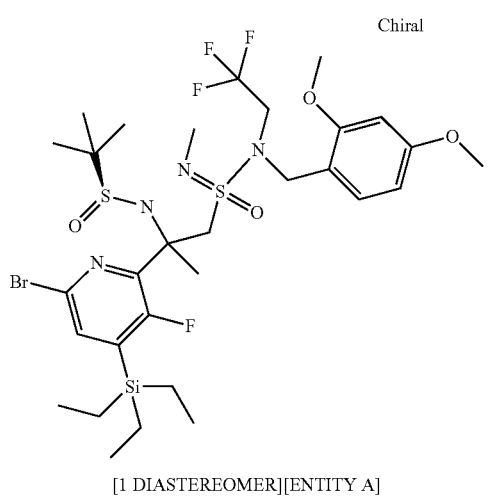

[1 DIASTEREOMER][ENTITY A]

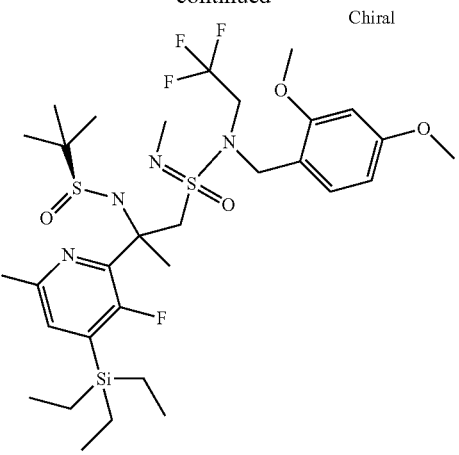

[1 DIASTEREOMER][ENTITY B]

To a solution of N-(2,4-dimethoxybenzyl)-N'-methyl-N-(2,2,2-trifluoroethyl)methanesulfonimidamide (2.08 g, 6.11 mmol, Eq: 1.4) in THF (24 ml) at −78° C. was added n-butyllithium (1.6N in hexane) (5.4 ml, 8.64 mmol, Eq: 1.98) dropwise. The clear solution was stirred at −78° C./−40° C. for 2.5 h (The reaction mixture was allowed to come after 1 h to −40° C., stirred at this temperature for 0.5 h and then at −78° C. for remaining time). A solution of (S,Z)—N-(1-(6-bromo-3-fluoro-4-(triethylsilyl)pyridin-2-yl)ethylidene)-2-methylpropane-2-sulfinamide (1.9 g, 4.36 mmol, Eq: 1) in THF (10 ml) was added dropwise (so that temperature remained at between −78° C. and −73° C.). The reaction mixture was stirred at −78° C. for 3 h, then quenched at −78° C. with 20 ml saturated aqueous $NH_4Cl$-solution and 30 ml water, followed by extraction with AcOEt (3×150 ml). The combined organic extracts were washed with brine, dried over $Na_2SO_4$, filtered off and evaporated to give a brownish oil. The crude material was purified by flash chromatography (silica gel, 80 g, 10% to 50% EtOAc in heptane) twice to yield the title compound ENTITY A (68 mg; 2%) and title compound ENTITY B (236 mg; 7%). m/z=777.199 [M+H]$^+$.

ENTITY A: $^1$H NMR (300 MHz, CHLOROFORM-d) ∈ ppm 0.82-1.01 (m, 17H) 0.83-0.84 (m, 1H) 1.31-1.33 (m, 1H) 1.35 (s, 9H) 1.85 (s, 3H) 2.47 (s, 3H) 3.80 (s, 1H) 3.82 (s, 3H) 3.83 (s, 3H) 4.44 (s, 2H) 6.45-6.48 (m, 2H) 6.45-6.48 (m, 1H) 6.46-6.51 (m, 2H) 7.22 (d, J=8.07 Hz, 1H) 7.30 (d, J=2.62 Hz, 1H) 7.36 (s, 1H)

ENTITY B: $^1$H NMR (300 MHz, CHLOROFORM-d) δ ppm 0.83-0.97 (m, 15H) 0.84-0.98 (m, 15H) 1.18-1.30 (m, 11H) 1.23-1.23 (m, 1H) 1.23-1.23 (m, 1H) 1.23-1.24 (m, 2H) 2.52-2.58 (m, 3H) 3.11 (d, J=13.72 Hz, 1H) 3.65-3.76 (m, 1H) 3.78-3.83 (m, 6H) 3.86-3.98 (m, 1H) 4.35-4.43 (m, 1H) 4.45-4.57 (m, 1H) 6.44-6.49 (m, 2H) 6.56-6.57 (m, 1H) 6.58 (s, 1H) 7.22 (d, J=8.07 Hz, 1H) 7.33 (d, J=2.62 Hz, 1H)

c) 2-Amino-2-(6-bromo-3-fluoro-4-(triethylsilyl)pyridin-2-yl)-N'-methyl-N-(2,2,2-trifluoroethyl)propane-1-sulfonimidamide

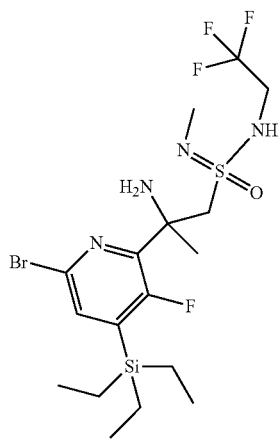 [SMILES: CC[Si](CC)(CC)c1cc(Br)nc(C(C)(N)CS(=O)(=NC)NCC(F)(F)F)c1F]

To a stirred solution of 2-(6-bromo-3-fluoro-4-(triethylsilyl)pyridin-2-yl)-N-(2,4-dimethoxybenzyl)-2-((S)-1,1-dimethylethylsulfinamido)-N'-methyl-N-(2,2,2-trifluoroethyl)propane-1-sulfonimidamide (0.1 g, 129 μmol, Eq: 1) in THF (0.5 ml) was added HCl (37% in water) (63.5 mg, 52.9 μl, 644 μmol, Eq: 5) at room temperature and stirred for 1 h. The crude mixture was evaporated and the residue was extracted with 10 ml AcOEt/3 ml saturated aqueous NaHCO₃-Solution, the aqueous layer was back-extracted with EtOAc (3×10 mL). The organic layers were combined, washed with saturated aqueous NaCl solution (1×3 mL), dried over MgSO₄ and concentrated in vacuo to yield the title compound as a light yellow gum (88 mg crude). m/z=523.2 [M+H]⁺.

d) N-[[2-(6-Bromo-3-fluoro-4-triethylsilylpyridin-2-yl)-1-[N-methyl-S-(2,2,2-trifluoroethylamino)sulfonimidoyl]propan-2-yl]carbamothioyl]benzamide

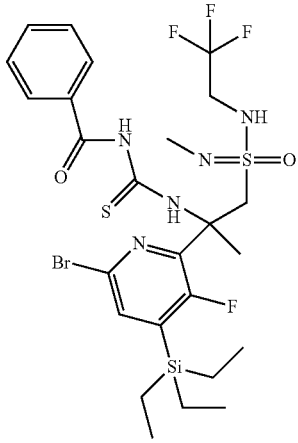 [SMILES: CC[Si](CC)(CC)c1cc(Br)nc(C(C)(CS(=O)(=NC)NCC(F)(F)F)NC(=S)NC(=O)c2ccccc2)c1F]

In a 10 ml flask 2-amino-2-(6-bromo-3-fluoro-4-(triethylsilyl)pyridin-2-yl)-N'-methyl-N-(2,2,2-trifluoroethyl)propane-1-sulfonimidamide (0.067 g, 128 μmol, Eq: 1 was combined with THF (800 μl) to give a light yellow solution. Benzoyl isothiocyanate (23.1 mg, 19 μl, 141 μmol, Eq: 1.1) was added and yellow solution was stirred at 25° C. for 1.5 h. The reaction mixture was evaporated. The crude material was purified subsequently by flash chromatography (silica gel, 4 g, 10% to 40% EtOAc in heptane) to yield the title compound as light yellow amorphous solid (44 mg; 50%). m/z=684.3 [M+H]⁺.

e) N-[(1R)-5-(6-bromo-3-fluoro-4-triethylsilylpyridin-2-yl)-5-methyl-1-methylimino-1-oxo-2-(2,2,2-trifluoroethyl)-6H-1,2,4-thiadiazin-3-yl]benzamide and N-[(1S)-5-(6-bromo-3-fluoro-4-triethylsilylpyridin-2-yl)-5-methyl-1-methylimino-1-oxo-2-(2,2,2-trifluoroethyl)-6H-1,2,4-thiadiazin-3-yl]benzamide (mixture of diastereomers)

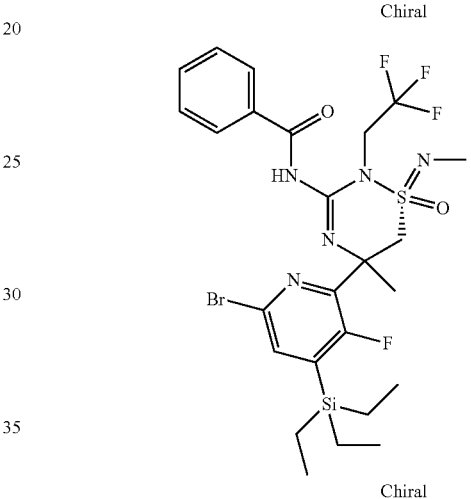

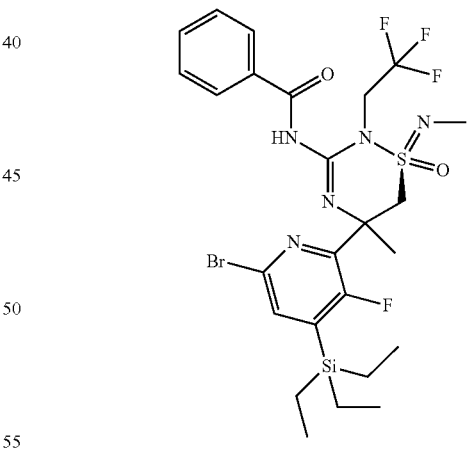

To a solution of N-[[2-(6-Bromo-3-fluoro-4-triethylsilylpyridin-2-yl)-1-[N-methyl-S-(2,2,2-trifluoroethylamino)sulfonimidoyl]propan-2-yl]carbamothioyl]benzamide in acetonitrile (0.7 ml) was added at room temperature N-1-((ethylimino)methylene)-N3,N3-dimethylpropane-1,3-diamine (14.3 mg, 16.3 μl, 92 μmol, Eq: 1.5) and the mixture was stirred at 80° C. for 1.5 h. The light yellow solution was evaporated. The crude material was purified by flash chromatography (silica gel, 4 g, 0% to 40% EtOAc in heptane) to yield the title compounds as colorless amorphous solid (22 mg; 55% and 10 mg; 25%). m/z=653.4 [M+H]⁺.

f) N-[5-(6-bromo-3-fluoropyridin-2-yl)-5-methyl-1-methylimino-1-oxo-2-(2,2,2-trifluoroethyl)-6H-1,2,4-thiadiazin-3-yl]benzamide

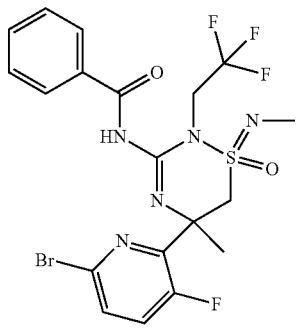 [SMILES: CN=S1(=O)CC(C)(c2nc(Br)ccc2F)N=C(NC(=O)c2ccccc2)N1CC(F)(F)F]

To a solution of N-(5-(6-bromo-3-fluoro-4-(triethylsilyl)pyridin-2-yl)-5-methyl-1-(methylimino)-1-oxido-2-(2,2,2-trifluoroethyl)-5,6-dihydro-2H-1,2,4-thiadiazin-3-yl)benzamide (0.180 g, 277 μmol, Eq: 1 in dry THF (1.8 ml) and DMF (1.8 ml) was added at 25° C. acetic acid (33.2 mg, 31.6 μl, 553 μmol, Eq: 2) and potassium fluoride (32.1 mg, 553 μmol, Eq: 2) and the formed white suspension was stirred at 25° C. for 1 h. The reaction mixture was evaporated, the residue was extracted with 7 ml AcOEt/3 ml aqueous saturated NaHCO₃-solution. The aqueous layer was back-extracted with EtOAc (3×5 ml). The organic layers were combined, washed with sat NaCl (1×5 ml), were dried over Na₂SO₄ and concentrated in vacuo to yield the title compound as a white solid (72 mg; 49%). m/z=538.2 [M+H]⁺.

g) tert-butyl N-[5-(6-bromo-3-fluoropyridin-2-yl)-5-methyl-1-methylimino-1-oxo-2-(2,2,2-trifluoroethyl)-6H-1,2,4-thiadiazin-3-yl]carbamate

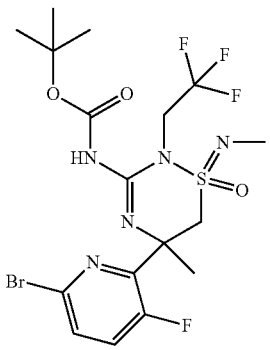 [SMILES: CN=S1(=O)CC(C)(c2nc(Br)ccc2F)N=C(NC(=O)OC(C)(C)C)N1CC(F)(F)F]

To a stirring solution of N-(5-(6-bromo-3-fluoropyridin-2-yl)-5-methyl-1-(methylimino)-1-oxido-2-(2,2,2-trifluoroethyl)-5,6-dihydro-2H-1,2,4-thiadiazin-3-yl)benzamide (0.085 g, 158 μmol, Eq: 1) in THF (1.0 ml) was added at 25° C. triethylamine (35.3 mg, 48.6 μl, 349 μmol, Eq: 2.2) and DMAP (19.4 mg, 158 μmol, Eq: 1) followed by the addition of di-tert-butyl dicarbonate (76.1 mg, 349 μmol, Eq: 2.2). The reaction mixture was stirred for 6 h. Additional di-tert-butyl dicarbonate (34.6 mg, 158 μmol, Eq: 1), DMAP (3.87 mg, 31.7 μmol, Eq: 0.2), triethylamine (16 mg, 22.1 μl, 158 μmol, Eq: 1) were added to the reaction mixture and stirred for further 1 h. The dark yellow crude reaction mixture was evaporated to dryness. The residue was dissolved in MeOH (1.0 ml) and ammonia (7 N in MeOH) (1.13 ml, 7.92 mmol, Eq: 50) was added at 25° C. The formed brownish solution was stirred for 25 min. The reaction mixture was evaporated and subsequently purified by flash chromatography (silica gel, 4 g, 0% to 30% EtOAc in heptane) to yield the title compound as a colorless foam (42 mg; 50%). m/z=534.2 [M+H]⁺.

h) tert-Butyl N-[5-(6-amino-3-fluoropyridin-2-yl)-5-methyl-1-methylimino-1-oxo-2-(2,2,2-trifluoroethyl)-6H-1,2,4-thiadiazin-3-yl]carbamate In a 10 mL round-bottomed flask, tert-butyl (5-(6-bromo-3-fluoropyridin-2-yl)-5-methyl-1-(methylimino)-1-oxido-2-(2,2,2-trifluoroethyl)-5,6-dihydro-2H-1,2,4-thiadiazin-3-yl)carbamate (0.045 g, 84.5 μmol, Eq: 1 was combined with dioxane (225 μl) and water (90 μl) to give a colorless solution. To this solution was added at 25° C. sodium azide (44 mg, 676 μmol, Eq: 8), copper (I) iodide (6.44 mg, 33.8 μmol, Eq: 0.4), sodium ascorbate (6.7 mg, 33.8 μmol, Eq: 0.4) followed by trans-N,N-dimethylcyclohexane-1,2-diamine (12 mg, 13.3 μl, 84.5 μmol, Eq: 1). The dark green reaction mixture was heated to 70° C. and stirred for 70 min. The reaction mixture was quenched with aqueous saturated NaHCO₃-solution and extracted 3× with AcOEt. The organic layers were combined and washed with saturated aqueous NaCl-solution, dried over Na₂SO₄ and concentrated in vacuo. The crude material was purified by flash chromatography (silica gel, 4 g, 5% to 40% EtOAc in heptane) to yield the title compound as an amorphous solid (15 mg; 38%). m/z=469.3 [M+H]⁺.

i) tert-butyl N-[5-[6-[(5-cyano-3-methylpyridine-2-carbonyl)amino]-3-fluoropyridin-2-yl]-5-methyl-1-methylimino-1-oxo-2-(2,2,2-trifluoroethyl)-6H-1,2,4-thiadiazin-3-yl]carbamate

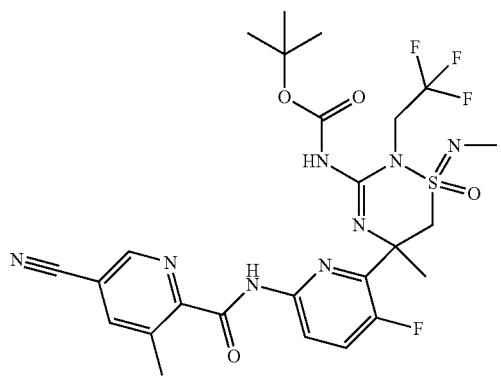 [SMILES: CN=S1(=O)CC(C)(c2nc(NC(=O)c3ncc(C#N)cc3C)ccc2F)N=C(NC(=O)OC(C)(C)C)N1CC(F)(F)F]

To a suspension of 5-cyano-3-methylpicolinic acid (7.89 mg, 48.7 µmol, Eq: 1.2) in dichloromethane (0.6 ml) was added at 0° C. 1-chloro-N,N,2-trimethylprop-1-en-1-amine (Ghosez's reagent) (6.77 mg, 6.71 µl, 50.7 µmol, Eq: 1.25) and the formed colorless solution was stirred at 0° C. for 15 min. A solution of tert-butyl (5-(6-amino-3-fluoropyridin-2-yl)-5-methyl-1-(methylimino)-1-oxido-2-(2,2,2-trifluoroethyl)-5,6-dihydro-2H-1,2,4-thiadiazin-3-yl)carbamate (0.019 g, 40.6 µmol, Eq: 1) in dichloromethane (800 µl) was added to above reaction mixture at 0° C. and the resulting yellow solution was allow to come to room temperature and stirred for 60 min. The reaction mixture was concentrated in vacuo. The residue was purified by flash chromatography (silica gel, 4 g, isocratically 40% AcOEt in n-heptane) to yield the title compound as white solid (8.8 mg; 35%). m/z=513.3 [M+H-Boc]$^+$.

j) N-[6-[3-amino-5-methyl-1-methylimino-1-oxo-2-(2,2,2-trifluoroethyl)-6H-1,2,4-thiadiazin-5-yl]-5-fluoropyridin-2-yl]-5-cyano-3-methylpyridine-2-carboxamide; 2,2,2-trifluoroacetic acid

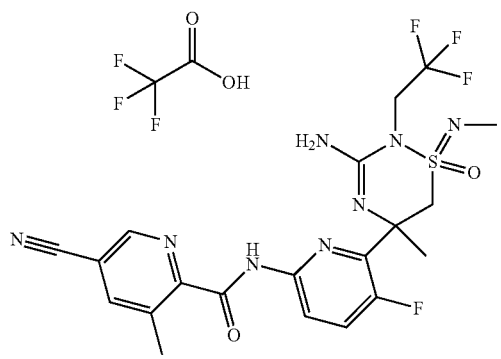 [SMILES: CN=S1(=O)CC(C)(c2nc(NC(=O)c3ncc(C#N)cc3C)ccc2F)N=C(N)N1CC(F)(F)F ; O=C(O)C(F)(F)F]

To a stirring solution of tert-butyl (5-(6-(5-cyano-3-methylpicolinamido)-3-fluoropyridin-2-yl)-5-methyl-1-(methylimino)-1-oxido-2-(2,2,2-trifluoroethyl)-5,6-dihydro-2H-1,2,4-thiadiazin-3-yl)carbamate (8.8 mg, 14.4 µmol, Eq: 1) in dichloromethane (110 µL) was added at 25° C. TFA (164 mg, 111 µL, 1.44 mmol, Eq: 100) and stirred for 30 min. The reaction mixture was concentrated in vacuo to yield the title compound as a colorless amorphous solid (8.43 mg; 94%). m/z=513.3 [M+H-TFA]$^+$.

Example 14: (5R)-5-(6-bromo-3-fluoropyridin-2-yl)-5-methyl-1-methylimino-1-oxo-2-(2,2,2-trifluoroethyl)-6H-1,2,4-thiadiazin-3-amine; 2,2,2-trifluoroacetic acid Example 14 was prepared in analogy to the methods described for example 13a)-13 g) and 13j) starting from (R,Z)—N-(1-(6-bromo-3-fluoro-4-(triethylsilyl)pyridin-2-yl)ethylidene)-2-methylpropane-2-sulfinamide to yield the title compound as a light yellow amorphous solid, m/z=434.1 [M+H-TFA]$^+$.

Example 15: N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]- 5-cyano-3-methylpyridine-2-carboxamide; 2,2,2-trifluoroacetic acid ([1 EPIMER][ENTITY B])

The title compound was prepared in analogy to the methods described for example 13a)-13j) starting from (R,Z)—N-(1-(6-bromo-3-fluoro-4-(triethylsilyl)pyridin-2-yl)ethylidene)-2-methylpropane-2-sulfinamide. m/z=434.1 [M+H-TFA]$^+$.

Example 16: N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]- 5-cyano-3-methylpyridine-2-carboxamide; 2,2,2-trifluoroacetic Acid ([1 EPIMER][ENTITY C])

The title compound was prepared in analogy to the methods described for example 13a)-13j) starting from (R,Z)—N-(1-(6-bromo-3-fluoro-4-(triethylsilyl)pyridin-2-yl)ethylidene)-2-methylpropane-2-sulfinamide. m/z=434.1 [M+H-TFA]$^+$.

Example 17: N-(6-((5R)-3-amino-5-methyl-1-(methylimino)-1-oxido-2-(2,2,2-trifluoroethyl)-5,6-dihydro-2H-1,2,4-thiadiazin-5-yl)-5- fluoropyridin-2-yl)-3-chloro-5-cyanopicolinamide ([1 EPIMER][ENTITY C])

The title compound was prepared in analogy to the methods described for example 13a)-13j) starting from (R,Z)—N-(1-(6-bromo-3-fluoro-4-(triethylsilyl)pyridin-2-yl)ethylidene)-2-methylpropane-2-sulfinamide. m/z=533.1/531.2 [M+H]$^+$. Cl-Isotopes.

Example 18: N-[6-[(5R)-3-amino-5-methyl-1-methylimino-1-oxo-2-(2,2,2-trifluoroethyl)-6H-1,2,4-thiadiazin-5-yl]-5-fluoropyridin-2-yl]- 5-fluoro-3-methylpyridine-2-carboxamide; 2,2,2-trifluoroacetic acid ([1 EPIMER][ENTITY C])

The title compound was prepared in analogy to the methods described for example 13a)-13j) starting from (R,Z)—N-(1-(6-bromo-3-fluoro-4-(triethylsilyl)pyridin-2-yl)ethylidene)-2-methylpropane-2-sulfinamide. m/z=506.2 [M+H-TFA]$^+$.

The invention claimed is:

1. A compound of formula I,

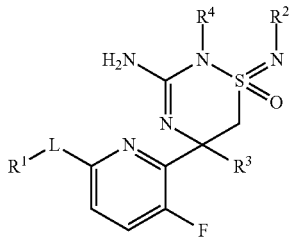

wherein $R^1$ is selected from the group consisting of
   i) H,
   ii) aryl,
   iii) aryl, substituted by 1-3 substituents individually selected from cyano, halogen, $C_{1-6}$-alkyl, halogen-$C_{1-6}$-alkyl and, —O—$C_{1-6}$-alkyl, —O—$C_{2-6}$-alkynyl, —O—$C_{1-6}$-alkyl-halogen
   iv) heteroaryl, and
   v) heteroaryl, substituted by 1-3 substituents individually selected from cyano, halogen, $C_{1-6}$-alkyl, halogen-$C_{1-6}$-alkyl, —O—$C_{1-6}$-alkyl, —O—$C_{2-6}$-alkynyl, and —O—$C_{1-6}$-alkyl-halogen;

$R^2$ is selected from the group consisting of
   i) $C_{1-6}$-alkyl, and
   ii) halogen-$C_{1-6}$-alkyl;

$R^3$ is selected from the group consisting of
   i) $C_{1-6}$-alkyl, and
   ii) halogen-$C_{1-6}$-alkyl;

$R^4$ is selected from the group consisting of
   i) $C_{1-6}$-alkyl, and
   ii) halogen-$C_{1-6}$-alkyl;

L is selected from the group consisting of
   i) absent, and
   ii) —NH—C(=O)—;

or a pharmaceutically acceptable salt thereof.

2. The compound according to claim 1, which is of formula Ia:

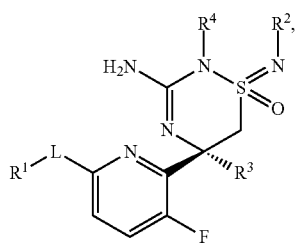

wherein L, $R^1$, $R^2$, $R^3$ and $R^4$ are as described in claim 1.

3. The compound according to claim 1, which is of formula Ia':

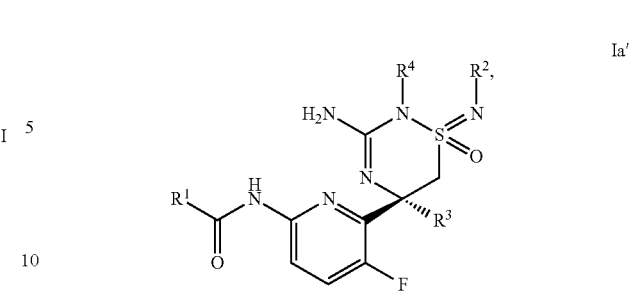

wherein L, $R^1$, $R^2$, $R^3$ and $R^4$ are as described in claim 1.

4. The compound according to claim 1, wherein $R^1$ is heteroaryl, substituted by 1-2 substituents individually selected from cyano, halogen, $C_{1-6}$-alkyl, halogen-$C_{1-6}$-alkyl, —O—$C_{1-6}$-alkyl, —O—$C_{2-6}$-alkynyl, and —O—$C_{1-6}$-alkyl-halogen.

5. The compound according to claim 1, wherein $R^1$ is pyridyl or pyrazinyl, substituted by 1-2 substituents individually selected from cyano, methyl, methoxy, fluoromethyoxy, trifluoroethoxy, but-2-ynoxy and prop-2-ynoxy.

6. The compound according to claim 1, wherein $R^1$ is 5-cyano-3-chloropyridyl, 5-cyano-3-methylpyridyl, 5-cyano-pyridyl, 5-fluoro-3-methylpyridyl, 5-(fluoromethoxy)pyridyl, 5-but-2-ynoxypyrazinyl, 5-methoxypyrazinyl, 5-(2,2,2-trifluoroethoxy)pyridyl, 5-prop-2-ynoxypyridyl.

7. The compound according to claim 1, wherein $R^1$ is 5-cyano-3-methylpyridyl, 5-cyano-pyridyl, 5-fluoro-3-methylpyridyl, 5-(fluoromethoxy)pyridyl, 5-but-2-ynoxypyrazinyl, 5-methoxypyrazinyl, 5-(2,2,2-trifluoroethoxy)pyridyl, 5-prop-2-ynoxypyridyl.

8. The compound according to claim 1, wherein $R^2$ is halogen-$C_{1-6}$-alkyl.

9. The compound according to claim 1, wherein $R^2$ is 2,2,2-trifluoroethyl.

10. The compound according to claim 1, wherein $R^2$ is $C_{1-6}$-alkyl.

11. The compound according to claim 1, wherein $R^2$ is methyl.

12. The compound according to claim 1, wherein $R^3$ is methyl.

13. The compound according to claim 1, wherein $R^4$ is methyl.

14. The compound according to claim 1, wherein $R^4$ is —$CH_2CF_3$.

15. An intermediate of formula I':

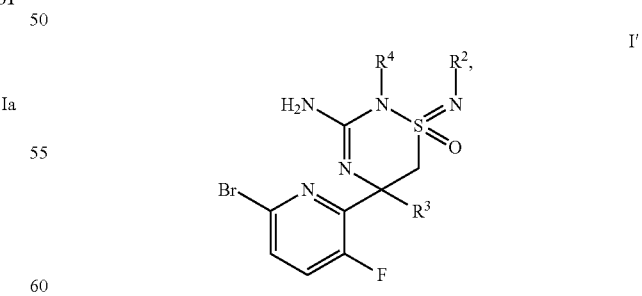

wherein $R^2$, $R^3$ and $R^4$ are as described in claim 1.

16. The compound according to claim 1, selected from the group consisting of:
(1R,5R)-5-(6-bromo-3-fluoro-2-pyridyl)-2,5-dimethyl-1-oxo-1-(2,2,2-trifluoroethylimino)-6H-1,2,4-thiadiazin-3-amine; 2,2,2-trifluoroacetic acid, (1R,5R)-5-[3-fluoro-6-(1H-pyrazol-5-yl)pyridin-2-yl]-2,
5-dimethyl-1-oxo-1-(2,2,2-trifluoroethylimino)-6H-1,
2,4-thiadiazin-3-amine, (1R,5R)-5-[6-(5-chlorothiophen-2-yl)-3-fluoropyridin-2-
yl]-2,5-dimethyl-1-oxo-1-(2,2,2-trifluoroethylimino)-
6H-1,2,4-thiadiazin-3-amine, (1S,5R)-5-(6-bromo-3-fluoropyridin-2-yl)-2,5-dimethyl-
1-oxo-1-(2,2,2-trifluoroethylimino)-6H-1,2,4-thiadi-
azin-3-amine; 2,2,2-trifluoroacetic acid, (5R)-5-(6-bromo-3-fluoropyridin-2-yl)-5-methyl-1-meth-
ylimino-1-oxo-2-(2,2,2-trifluoroethyl)-6H-1,2,4-thia-
diazin-3-amine; 2,2,2-trifluoroacetic acid, N-(6-((5R)-3-amino-5-methyl-1-(methylimino)-1-oxido-
2-(2,2,2-trifluoroethyl)-5,6-dihydro-2H-1,2,4-thiadi-
azin-5yl)-5-fluoropyridin-2-yl)-3-chloro-5-cyanopico-
linamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-cyano-3-methylpyridine-2-carboxam-
ide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-cyanopyridine-2-carboxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-fluoro-3-methylpyridine-2-carboxam-
ide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-(fluoromethoxy)pyridine-2-carboxam-
ide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-but-2-ynoxypyrazine-2-carboxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-methoxypyrazine-2-carboxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-(2,2,2-trifluoroethoxy)pyridine-2-car-
boxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-prop-2-ynoxypyridine-2-carboxamide, N-[6-[(5R)-3-amino-5-methyl-1-methylimino-1-oxo-2-
(2,2,2-trifluoroethyl)-6H-1,2,4-thiadiazin-5-yl]-5-fluo-
ropyridin-2-yl]-5-cyano-3-methylpyridine-2-carbox-
amide, N-[6-[(5R)-3-amino-5-methyl-1-methylimino-1-oxo-2-
(2,2,2-trifluoroethyl)-6H-1,2,4-thiadiazin-5-yl]-5-fluo-
ropyridin-2-yl]-5-cyano-3-methylpyridine-2-carbox-
amide, N-[6-[(5R)-3-amino-5-methyl-1-methylimino-1-oxo-2-
(2,2,2-trifluoroethyl)-6H-1,2,4-thiadiazin-5-yl]-5-fluo-
ropyridin-2-yl]-5-fluoro-3-methylpyridine-2-carboxy-
amide, and N-[6-[3-amino-5-methyl-1-methylimino-1-oxo-2-(2,2,2-
trifluoroethyl)-6H-1,2,4-thiadiazin-5-yl]-5-fluoropyri-
din-2-yl]-5-cyano-3-methylpyridine-2-carboxamide, or a pharmaceutically acceptable salt thereof.

17. The compound according to claim 1, selected from the group consisting of:

(1R,5R)-5-(6-bromo-3-fluoro-2-pyridyl)-2,5-dimethyl-1-
oxo-1-(2,2,2-trifluoroethylimino)-6H-1,2,4-thiadiazin-
3-amine, (1S,5R)-5-(6-bromo-3-fluoropyridin-2-yl)-2,5-dimethyl-
1-oxo-1-(2,2,2-trifluoroethylimino)-6H-1,2,4-thiadi-
azin-3-amine, N-[6-[(1R,5R)-3-amino-2,5-dimethyl-1-oxo-1-(2,2,2-trif-
luoroethylimino)-6H-1 2,4-thiadiazin-5-yl]-5-fluoro-
pyridin-2-yl]-5-cyano-3-methylpyridine-2-carboxam-
ide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-cyanopyridine-2-carboxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-fluoro-3-methylpyridine-2-carboxam-
ide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-(fluoromethoxy)pyridine-2-carboxam-
ide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-but-2-ynoxypyrazine-2-carboxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-methoxypyrazine-2-carboxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-(2,2,2-trifluoroethoxy)pyridine-2-car-
boxamide, N-[6-[(1R,5R)-3-amino-2,5-dimethyl-1-oxo-1-(2,2,2-trif-
luoroethylimino)-6H-1,2,4-thiadiazin-5-yl]-5-fluoro-
pyridin-2-yl]-5-prop-2-ynoxypyridine-2-carboxamide, (1R,5R)-5-[3-fluoro-6-(1H-pyrazol-5-yl)pyridin-2-yl]-2,
5-dimethyl-1-oxo-1-(2,2,2-trifluoroethylimino)-6H-1,
2,4-thiadiazin-3-amine, and (1R,5R)-5-[6-(5-chlorothiophen-2-yl)-3-fluoropyridin-2-
yl]-2,5-dimethyl-1-oxo-1-(2,2,2-trifluoroethylimino)-
6H-1,2,4-thiadiazin-3-amine, or a pharmaceutically acceptable salt thereof.

18. A method for the treatment of Alzheimer's disease, comprising the step of administering a therapeutically effective amount of a compound according to claim 1, or a pharmaceutically acceptable salt thereof, to a patient in need thereof.

19. A process for the preparation of a compound according to claim 1, comprising the step of reacting a compound of formula XI' with a compound of formula XII':

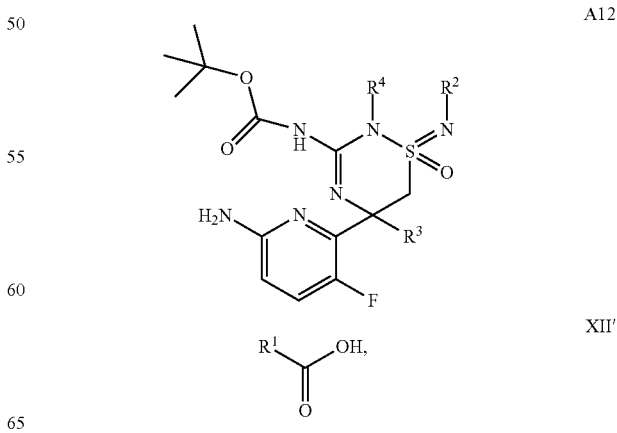

wherein $R^1$, $R^2$, $R^3$ and $R^4$ are as defined in claim 1.

20. A pharmaceutical composition, comprising a therapeutically effective amount of a compound according to claim 1, or a pharmaceutically acceptable salt thereof, and a pharmaceutically acceptable excipient.

* * * * *